United States Patent
Chan et al.

(10) Patent No.: US 7,705,222 B2
(45) Date of Patent: *Apr. 27, 2010

(54) CONTROLLED ALIGNMENT OF NANO-BARCODES ENCODING SPECIFIC INFORMATION FOR SCANNING PROBE MICROSCOPY (SPM)

(75) Inventors: Selena Chan, San Jose, CA (US); Xing Su, Cupertino, CA (US); Mineo Yamakawa, Campbell, CA (US)

(73) Assignee: Intel Corporation, Santa Clara, CA (US)

( * ) Notice: Subject to any disclaimer, the term of this patent is extended or adjusted under 35 U.S.C. 154(b) by 406 days.

This patent is subject to a terminal disclaimer.

(21) Appl. No.: 11/446,273

(22) Filed: Jun. 2, 2006

(65) Prior Publication Data

US 2006/0281119 A1   Dec. 14, 2006

Related U.S. Application Data

(60) Division of application No. 10/667,004, filed on Sep. 19, 2003, now Pat. No. 7,476,786, which is a continuation-in-part of application No. 10/251,152, filed on Sep. 20, 2002, now Pat. No. 7,361,821.

(51) Int. Cl.
*C07H 21/02* (2006.01)
*C07H 21/04* (2006.01)
*C12M 1/00* (2006.01)
*C12M 1/34* (2006.01)
*C12M 3/00* (2006.01)

(52) U.S. Cl. .............. 977/704; 977/728; 977/734; 977/742; 977/773; 977/774; 536/23.1; 536/24.3; 536/24.33; 435/283.1; 435/287.1; 435/287.2

(58) Field of Classification Search .............. 435/6, 435/91.1, 183, 283.1, 287.1, 287.2; 436/94, 436/501; 536/23.1, 24.3, 24.33; 977/702, 977/704, 728, 734, 773

See application file for complete search history.

(56) References Cited

U.S. PATENT DOCUMENTS

| | | | |
|---|---|---|---|
| 3,772,200 A | 11/1973 | Livesay | |
| 4,053,433 A | 10/1977 | Lee | 252/408 |
| 4,683,195 A | 7/1987 | Mullis | |
| 4,683,202 A | 7/1987 | Mullis | |
| 4,800,159 A | 1/1989 | Mullis | |
| 5,401,511 A | 3/1995 | Margalit | |
| 5,405,766 A | 4/1995 | Kallury | |
| 5,451,505 A | 9/1995 | Dollinger | 435/6 |
| 5,472,881 A | 12/1995 | Beebe | |
| 5,538,898 A | 7/1996 | Wickramasinghe et al. | 436/94 |
| 5,603,872 A | 2/1997 | Margalit | |
| 5,610,287 A | 3/1997 | Nikiforov et al. | |
| 5,620,854 A | 4/1997 | Holzrichter et al. | |
| 5,776,674 A | 7/1998 | Ulmer | |
| 5,840,862 A | 11/1998 | Bensimon et al. | |
| 5,986,076 A | 11/1999 | Rothschild | |
| 6,013,456 A | 1/2000 | Khavan-Tafti | |
| 6,054,327 A | 4/2000 | Bensimon et al. | |
| 6,187,823 B1 | 2/2001 | Haddon | |
| 6,225,055 B1 | 5/2001 | Bensimon et al. | |
| 6,225,068 B1 | 5/2001 | Wolfrum | |
| 6,248,537 B1 | 6/2001 | Bensimon | |
| 6,258,401 B1 | 7/2001 | Crowley | |
| 6,265,153 B1 | 7/2001 | Bensimon et al. | |
| 6,280,939 B1 | 8/2001 | Allen | |
| 6,283,812 B1 | 9/2001 | Jin | |
| 6,297,592 B1 | 10/2001 | Goren | |
| 6,303,094 B1 | 10/2001 | Kusunoki | |
| 6,303,296 B1 | 10/2001 | Bensimon et al. | |
| 6,319,670 B1 | 11/2001 | Sigal et al. | |
| 6,344,319 B1 | 2/2002 | Bensimon et al. | |
| 6,358,375 B1 | 3/2002 | Schwob | |
| 6,361,944 B1 | 3/2002 | Mirkin et al. | 435/6 |
| 6,432,715 B1 | 8/2002 | Nelson et al. | 435/56 |
| 6,459,758 B1 | 10/2002 | Lee et al. | |
| 6,537,755 B1 | 3/2003 | Drmanac | 435/6 |
| 7,169,275 B2 | 1/2007 | Eckerskorn et al. | |
| 7,361,821 B2* | 4/2008 | Chan et al. | 435/6 |

(Continued)

FOREIGN PATENT DOCUMENTS

| | | |
|---|---|---|
| WO | WO 92/15709 | 9/1992 |
| WO | WO97/15390 | 5/1997 |
| WO | WO 98/04740 | 2/1998 |
| WO | WO 00/29617 | 5/2000 |
| WO | WO 00/68692 | 11/2000 |
| WO | WO 01/25002 | 4/2001 |
| WO | WO 02/32404 | 4/2002 |

OTHER PUBLICATIONS

Attachment on Free Flow Electrophoresis. http://aesociety.org/areas/ffe1.php. Accessed Oct. 23, 2007.

(Continued)

*Primary Examiner*—Frank W Lu
(74) *Attorney, Agent, or Firm*—Pillsbury Winthrop Shaw Pittman LLP

(57) ABSTRACT

The methods, apparatus and compositions disclosed herein concern the detection, identification and/or sequencing of biomolecules, such as nucleic acids or proteins. In certain embodiments of the invention, coded probes comprising a probe molecule attached to one or more nano-barcodes may be allowed to bind to one or more target molecules. After binding and separation from unbound coded probes, the bound coded probes may be aligned on a surface and analyzed by scanning probe microscopy. Where the probes are oligonucleotides, adjacent coded probes hybridized to a target nucleic acid may be ligated together before alignment and SPM analysis. Compositions comprising coded probes are also disclosed herein. Systems for biomolecule analysis may comprise an SPM instrument and at least one coded probe attached to a surface.

10 Claims, 15 Drawing Sheets

U.S. PATENT DOCUMENTS

| | | | |
|---|---|---|---|
| 2002/0034827 A1 | 3/2002 | Singh et al. | |
| 2002/0146714 A1* | 10/2002 | Lieber et al. | 435/6 |
| 2003/0148793 A1 | 8/2003 | Sundararajan et al. | |
| 2003/0165935 A1 | 9/2003 | Vann et al. | |

OTHER PUBLICATIONS

Blondel, et al., "Giant Magnetoresistance of Nanowires of Multilayers", *Am Inst of Phys.* 65(23):3018-3021, (Dec. 5, 1994).
Martin, et al., "Orthogonal Self-Assembly on Colloidal Gold-Platinum Nanorods", *Adv Mat.* 11(12)1021-1025, (1999).
Martin, Charles, "Membrane-Based Synthesis of Nanomaterials", *Chem. Mater.* 8:1739-1746, (1996).
Piraux, et al., "Giant Magnetorsistance in Magnetic Multilayered Nanowires", *Appl. Phys. Lett.* 65(19):2484-2486, (1994).
Definition of "Barcode". http://en.wikipedia.org/wiki/Barcode. Accessed Jul. 9, 2007.
Adjari, et al. (1991). "Free-floe Electrophoresis with Trapping by a Transverse Inhomogeneous Field," *Proc. Natl. Acad. Sci.* 88:4468-4471.
Ando, et al. (2001). "A High-Speed Atomic Force Microscope for Studying Biological Macromolecules," *PNAS* 98(22):12468-12472.
Bensimon, et al. (1994). "Alignment and Sensitive Detection of DNA by a Moving Interface," *Science* 265:2096-2098.
Bensimon, et al. (1995). "Stretching DNA with a Receding Meniscus: Experiments and Models," *Physical Review Letters* 74(23):4754-4757.
Clauss, et al. (1998). "Atomic resolution STM Imaging of a twisted Single-Wall Carbon Nanotube," *Physical Review B* 58(8):4266-4269.
Clauss, et al. (1999). "Electron Backscattering on Single-Wall Carbon Nanotubes Observed by Scanning Tunneling Microscopy," *Europhys Lett.* 47(5):601-607.
Freitag, et al. (2000). "Local Electronic Properties of a Single-Wall nanotube circuits Measured by Conducting-Tip AFM, " *Physical Review B* 62(4):2307-2310.
Frisbie, et al. (1994). "Functional Group Imaging by Chemical Force Microscopy," *Science* 263:2071-2074.
Gerdes et al. (1999). "Combing a Carbon Nanotube on a Flat Metal-Insulator-Metal Nanojunction, " *Europhys Lett.* 48(3):292-298.
Herrick et al. (2000). "Ouantifying Single Genre Copy Number by Measuring Fluorescent Probe Lengths on Combed Genomic DNA," *PNAS* 97(1):222-227.
Hirahara et al. (2000). "One-Dimensional Metallofullerene Crystal Generated Inside Single-Walled Carbon Nanotubes," *Physical Review Letters* 85(25):5384-5387.
Hu et al. (1996). "Imaging of Single Extended DNA Molecules on Flate (Aminopropyl)triethoxysilane Mica by Atomic Force Microscopy," *Langmuir* 12(7):1697-1700.

Huang et al. (2001) "Directed Assembly of One-Dimensional Nanostructures into Functional Networks," *Science* 291:630-633.
Kaczorowski et al. (1996) "Co-Operativity of Hexamer Litigation," *Gene* 179:189-193.
Kim et al. (1998). "AFM Study of Surface Phenomena Based on $C_{60}$ Film Growth," *Applied Surface Science* 130-132:602-609.
Klien et al. (2001). "Ordered Stretching of Single Molecules of Deoxyribose Nucleic Acid Between Microfabricated Polystyrene Lines," *Applied Physics Letters* 78(16):2396-2398.
Kobayashi et al. (2000). "Imaging of Fullerene Molecules on Si(111)-7 7 Surface withNC-AFM," *Applied Surface Science* 157:228-232.
Kotler et al. (1993). "DNA Sequencing: Modular Primers Assembled from a Library of Hexamers or Pentamers," *Proc. Natl. Acad. Sci.* 90:4241-4245.
Liu et al. (1998). "Fullerene Pipes," *Science* 280:1253-1256.
Michalet et al. (1997). "Dynamic Molecular Combing: Stretching the Whole Human Genome for High-Resolution Studies," *Science* 277:1518-1523.
Nicewarmer-Pena (2001). "Submicrometer Metallic Barcodes," *Science* 294:137-141.
Odom et al. (2002). "Single-Walled Carbon Nanotubes," *Ann. N.Y. Acad. Sci.* 960:203-215.
Ondarcuhu et al. (2000). "Parallel Fabrication and electrical Characterisation of Carbon Nanotube Hybrid Molecular Devices," 2 pages.
Shoenfeld et al. (1996). "Formation Si Quantum Dots in Nanocrystalline Silicon," *Solid-State Electronics* 40(1-8):605-608.
Uchihashi et al. "Application of Noncontact-mode Atomic Force Microscopy to Molecular Imaging," located at <http://foresight.org/Conferences/MNT7/Abstracts/Uchihashi/> visited on Jul. 3, 2002. (2 pages).
Wildöer et al. (1998) "Electronic Structure of Atomically Resolved Carbon Nanotubes," *Nature* 391:59-62.
Woolley et al. (2000). "Direct Haplotyping of Kilobase-SizeDNA Using Carbon Nanotube Probes," *Nature Biotechnology*, 18:760-763.
Li, "Biological Application of AFM," located at <http://www.chembio.uoguelph.ca/educmat/chm/729afm/applicat.htm> visited on Jul. 12, 2002. (2 pages).
"Carbon Nanotubes," <http://1rsm.upenn.edu/nanophysics/nanotubes.html> visited Jul. 2, 2002. (2 pages).
Fischer et al. "Carbon Nanotube-Derived Materials," located at <http://1rsm.upenn.edu/1rsm/IRG_2.pdf> visited Jul. 12, 2002. (pp. 32-41).
Venema et al. "Imaging Electron Wave Functions of Quantized Energy Levels in Carbon Nanotubes," Science, 283, 52-55, 1999.
Boutorine, A. (1995). "Fullerene-Oligionucleotide Conjugates: Photo-Induced Sequece-Specific DNA Cleavage," *Angewandte Chemie.* 33(23/24):2462-2465.

\* cited by examiner

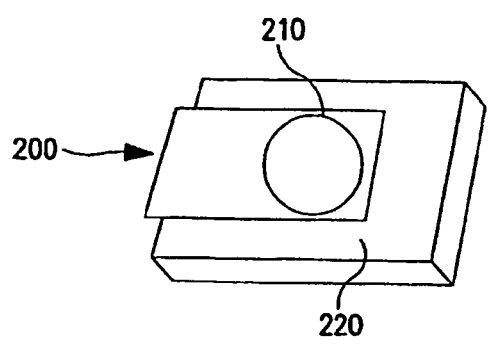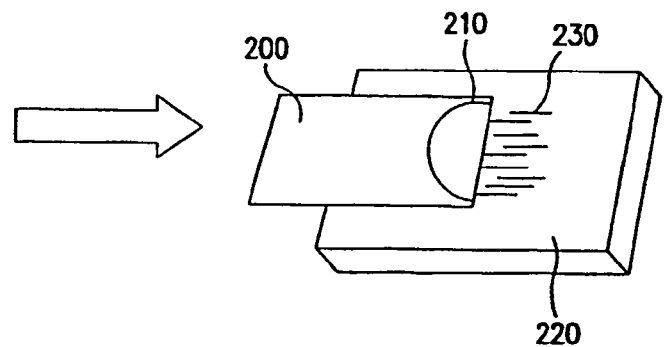
FIG. 2A                    FIG. 2B

FIG. 5
(A)
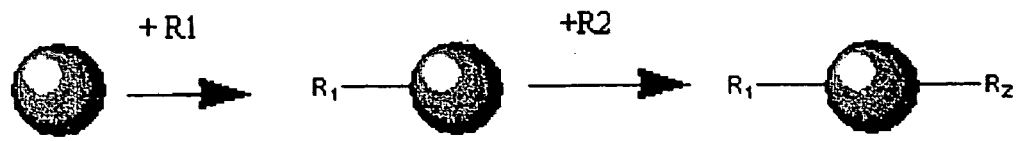
(B)
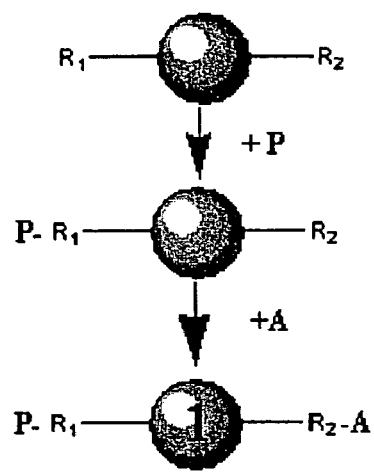
(C)
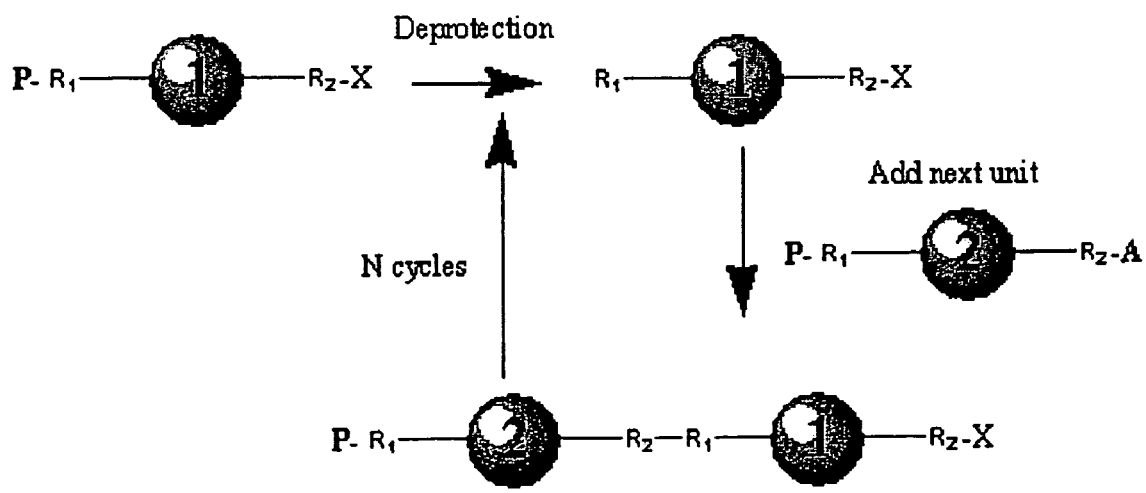

FIG. 6
(A)
(B)
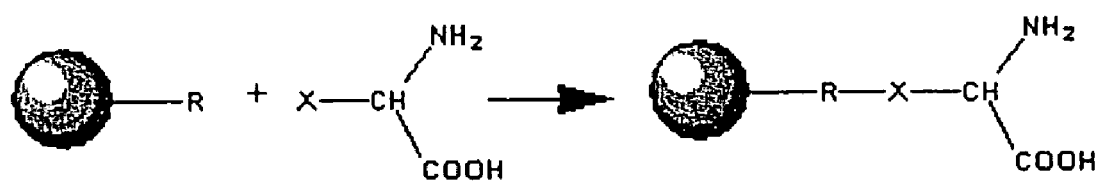
(C)
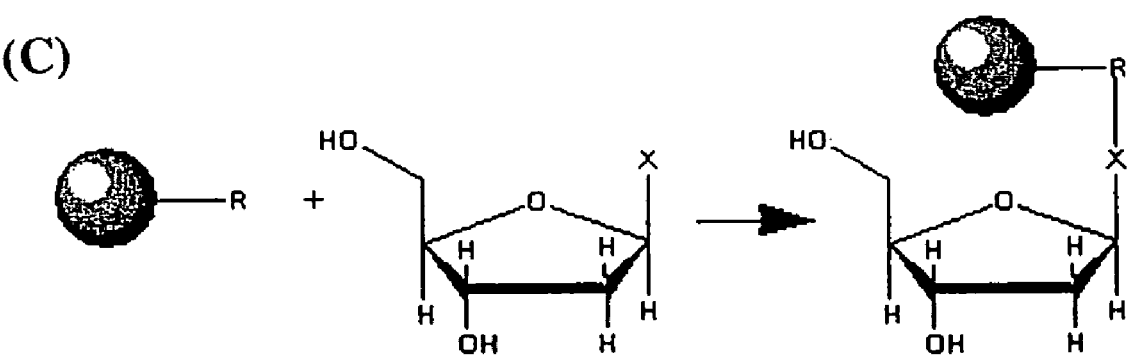

FIG. 14

PT1 TTGGGTACACTTACCTGTACCCCACCCGGAGTTAGGGGC (SEQ ID NO:3)

PT2 GCCCCTAACTGTGGAAAATCGATGGGCCCGCGGCCGCTCTTATGGTTGCTGACTAGACCA (SEQ ID NO:4)

PT3 TGGTCTAGTCAGCAACCATATAAGAAGTACTCTCGAGAAGCTTTTTGAATTCTTTGGATCCATGGGGGCGGAG (SEQ ID NO:5)

PT4 CTCCGCCCCACTAGTGTCGACCTGCAGGCGCGAGCTCCAATGGGCGACAATGGCACA (SEQ ID NO:6)

PT5 TGTGCCATTGTCCGCCCATTAGCTTTTGTTCCCTTTAGTGAGGGTTAATTTCGAGCTTGGATTGAGATGC (SEQ ID NO:7)

PT6 GCATCTCAATCGTAATCAAGGTCATAGCTGTGTTCCTGTGTTTGCATACTTCTGCCATTCG (SEQ ID NO:8)

PT7 CGAATGGCAGAAGTATGCAAGAGAAATTGTTATCCGCTCACAATTCCACACAATATACGAGCTGCTGGGGAG (SEQ ID NO:9)

PT8 CTCCCCAGCACGGAAGTAAAGCTTGGGGTGCGGATGGGCGGAATGAGACTG (SEQ ID NO:10)

PT9 ACAGTCTCATTCCGCCCATCCCTAATGAGTGAGCTAACTCACAGTAATTGCGGCTAGCGGA (SEQ ID NO:11)

CONTROLLED ALIGNMENT OF NANO-BARCODES ENCODING SPECIFIC INFORMATION FOR SCANNING PROBE MICROSCOPY (SPM)

CROSS-REFERENCE TO RELATED APPLICATION

This application is a divisional application of U.S. application Ser. No. 10/667,004 filed Sep. 19, 2003, now U.S. Pat. No. 7,476,786; which is a continuation-in-part application of U.S. application Ser. No. 10/251,152 filed Sep. 20, 2002, now U.S. Pat. No. 7,361,821. The disclosure of each of the prior applications is considered part of and is incorporated by reference in the disclosure of this application.

FIELD OF THE INVENTION

The present methods, compositions and apparatus relate to the fields of molecular biology and analysis of biomolecules including, but not limited to, nucleic acids, proteins, lipids and polysaccharides. In particular, the invention relates to methods, compositions and apparatus for detection, identification and/or sequencing of nucleic acids and/or other biomolecules using nano-barcodes and scanning probe microscopy (SPM).

BACKGROUND

Identification and/or sequencing of biomolecules, such as nucleic acids or proteins, is essential for medical diagnostics, forensics, toxicology, pathology, biological warfare, public health and numerous other fields. Although a great deal of research is presently directed towards identification and/or sequencing of nucleic acids or proteins, other biomolecules such as carbohydrates, polysaccharides, lipids, fatty acids, etc. may be of importance. The methods, compositions and apparatus disclosed herein are not limited to identification and/or sequencing of nucleic acids, but are also of use for analysis of other types of biomolecules, including but not limited to proteins, lipids and polysaccharides.

Standard methods for nucleic acid detection, such as Southern blotting or binding to nucleic acid chips, rely on hybridization of a fluorescent or radioactive probe molecule with a target nucleic acid molecule. Known methods for nucleic acid sequencing typically utilize either the Sanger dideoxy technique or hybridization to nucleic acid chips.

Oligonucleotide hybridization based assays are in wide use for detection of target nucleic acids. A probe oligonucleotide that is complementary in sequence to a target nucleic acid is attached to a fluorescent, radioactive or other moiety and allowed to hybridize to a nucleic acid through Watson-Crick base pair formation. Many variations on this technique are known. More recently, DNA chips have been designed that can contain hundreds or even thousands of oligonucleotide probes. Hybridization of a target nucleic acid to an oligonucleotide on a chip may be detected using fluorescence spectroscopy, radioactivity, etc. Problems with sensitivity and/or specificity may result from nucleic acid hybridization between sequences that are not precisely complementary. The presence of low levels of a target nucleic acid in a sample may not be detected.

Methods for Sanger dideoxy nucleic acid sequencing, based on detection of four-color fluorescent or radioactive nucleic acids that have been separated by size, are limited by the length of the nucleic acid that can be sequenced. Typically, only 500 to 1,000 bases of nucleic acid sequence can be determined at one time. Using current methods, determination of a complete gene sequence requires that many copies of the gene be produced, cut into overlapping fragments and sequenced, after which the overlapping DNA sequences may be assembled. This process is laborious, expensive, inefficient and time-consuming. It also typically requires the use of fluorescent or radioactive moieties, which can potentially pose safety and waste disposal problems. More recent methods for nucleic acid sequencing using hybridization to oligonucleotide chips may be used to infer short nucleic acid sequences or to detect the presence of a specific nucleic acid in a sample, but are not suited for identifying long nucleic acid sequences.

A variety of techniques are available for identification of proteins, polypeptides and peptides. Commonly, these involve binding and detection of antibodies that can recognize one or more epitopic domains on the protein. Although antibody-based identification of proteins is fairly rapid, such assays may occasionally show unacceptably high levels of false positive or false negative results, due to cross-reactivity of the antibody with different antigens, low antigenicity of the target analyte (leading to low sensitivity of the assay), non-specific binding of antibody to various surfaces, etc. They also require the preparation of antibodies that can recognize an individual protein or peptide. As such, they are not suitable for the identification of novel proteins that have not previously been characterized.

A need exists for rapid, accurate and sensitive methods for detection, identification and/or sequencing of biomolecules, such as nucleic acids or proteins.

BRIEF DESCRIPTION OF THE DRAWINGS

The following drawings form part of the present specification and are included to further demonstrate certain aspects of the disclosed embodiments of the invention. The embodiments of the invention may be better understood by reference to one or more of these drawings in combination with the detailed description of specific embodiments presented herein.

FIG. 2 illustrates an alternative exemplary method for aligning coded probes 230 on a surface 220. (A) A drop of solution 210 containing coded probes 230 is sandwiched between a cover slip 200 and a glass slide 220. (B) While the cover slip 200 is held in place, the slide 220 is moved, resulting in alignment of the coded probes 230.

FIG. 5 shows an exemplary scheme for synthesis of coded probes. (A) Conversion of exemplary nano-tag element into a bi-functional molecule containing R1 and R2 functional moieties. (B) Protection of one functional moiety and activation of the other. (C) Stepwise addition of building blocks in a controlled polymerization.

FIG. 6 illustrates a general scheme for backbone mediated nano-barcode synthesis. (A) Monofunctionalization of tag unit. (C) Conversion to nucleotide analog. (B) Conversion to amino acid analog.

FIG. 14 lists the complete sequences of PT1 through FT9, including the branch points.

DESCRIPTION OF ILLUSTRATIVE EMBODIMENTS

Figure 1A:
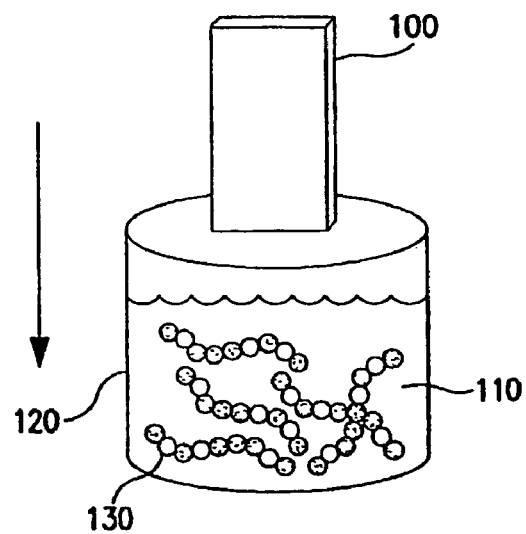
FIG. 1 illustrates an exemplary method for aligning coded probes 130, each comprising one or more nano-barcodes attached to a probe molecule on a surface 100. (A) Immersion of a surface 100 into a solution 110 containing coded probes 130. (B) Removal of the surface 100 containing aligned coded probes 130 from solution 110.
Figure 1B:
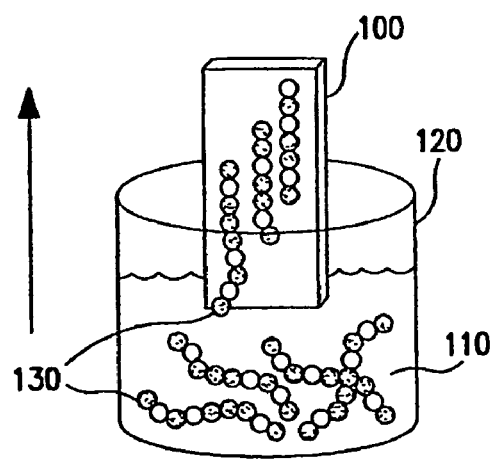

The disclosed methods, compositions and apparatus are of use for detection, identification and/or sequencing of biomolecules, such as nucleic acids. In particular embodiments of the invention, the methods, compositions and apparatus are suitable for obtaining the sequences of very long nucleic acid molecules of greater than 1,000, greater than 2,000, greater than 5,000, greater than 10,000 greater than 20,000, greater than 50,000, greater than 100,000 or even more bases in length. Advantages include the ability to read long nucleic acid sequences in a single sequencing run, high speed of obtaining sequence data, low cost of sequencing and high efficiency in terms of the amount of operator time required per unit of sequence data. Other advantages include the sensitive and accurate detection and/or identification of nucleic acids, with low incidence of false positive results.

The following detailed description contains numerous specific details in order to provide a more thorough understanding of the disclosed embodiments of the invention. However, it will be apparent to those skilled in the art that the embodiments of the invention may be practiced without these specific details. In other instances, devices, methods, procedures, and individual components that are well known in the art have not been described in detail herein.

Definitions

As used herein, "a" or "an" may mean one or more than one of an item.

"Nucleic acid' encompasses DNA, RNA (ribonucleic acid), single-stranded, double-stranded or triple stranded and any chemical modifications thereof. Virtually any modification of the nucleic acid is contemplated. A "nucleic acid" may be of almost any length, from oligonucleotides of 2 or more bases up to a full-length chromosomal DNA molecule. Nucleic acids include, but are not limited to, oligonucleotides and polynucleotides.

"Coded probe" refers to a probe molecule attached to one or more nano-barcodes. A probe molecule is any molecule that exhibits selective and/or specific binding to one or more target molecules. In various embodiments of the invention, each different probe molecule may be attached to a distinguishable nano-barcode, so that binding of a particular probe from a population of different probe molecules may be detected. The embodiments of the invention are not limited as to the type of probe molecules that may be used. Any probe molecule known in the art, including but not limited to oligonucleotides, nucleic acids, antibodies, antibody fragments, binding proteins, receptor proteins, peptides, lectins, substrates, inhibitors, activators, ligands, hormones, cytokines, etc. may be used. In certain embodiments of the invention, coded probes may comprise oligonucleotides and/or nucleic acids that have been covalently or non-covalently attached to one or more nano-barcodes that identify the sequence of the oligonucleotide and/or nucleic acid. In various embodiments of the invention, a linear series of coded probes may be ligated together. Each coded probe in the ligated molecule may be attached to a distinguishable nano-barcode to allow identification of its sequence. Since the sequence of coded probes in a ligated molecule may also be determined, the sequence of the entire ligated molecule may be identified. In alternative embodiments, each nucleotide within an oligonucleotide probe may be attached to a distinguishable nano-barcode, allowing the sequence of the coded probe to be identified from the sequence of nucleotides.

"Nano-barcode" refers to a composition that may be used to detect and/or identify a coded probe. In non-limiting examples discussed in more detail below, a nano-barcode may comprise one or more submicrometer metallic barcodes, carbon nanotubes, fullerenes or any other nanoscale moiety that may be detected and identified by scanning probe microscopy. Nano-barcodes are not limited to single moieties and in certain embodiments of the invention a nano-barcode may comprise, for example, two or more fullerenes attached to each other. Fullerenes for example may consist of a series of large and small fullerenes attached together in a specific order. The order of differently sized fullerenes in a nano-barcode may be detected by scanning probe microscopy and used, for example, to identify the sequence of an attached oligonucleotide probe.

A "target" or "analyte" molecule is any molecule that may bind to a coded probe, including but not limited to nucleic acids, proteins, lipids and polysaccharides. In some embodiments of the invention, binding of a coded probe to a target molecule may be used to detect the presence of the target molecule in a sample.

Molecular Combing

In various embodiments of the invention, nano-barcodes, coded probes and/or target molecules bound to coded probes may be attached to a surface and aligned for analysis. Alignment of the coded probes provides for an increased accuracy and/or speed of coded probe identification. Coded probes or nano-barcodes that are placed upon a surface in a disorganized pattern may overlap with each other or be partially obscured, complicating their detection and/or identification. In some embodiments, coded probes may be aligned on a surface and the incorporated nano-barcodes detected as discussed below. In alternative embodiments, nano-barcodes may be detached from the probe molecules, aligned on a surface and detected. In certain embodiments, the order of coded probes bound to an individual target molecule may be retained and detected, for example, by scanning probe microscopy. In other embodiments, multiple copies of a target molecule may be present in a sample and the identity and/or sequence of the target molecule may be determined by assembling all of the sequences of coded probes binding to the multiple copies into an overlapping target molecule sequence. Methods for assembling, for example, overlapping partial nucleic acid or protein sequences into a contiguous sequence are known in the art. In various embodiments, nano-barcodes may be detected while they are attached to probe molecules, or may alternatively be detached from the probe molecules before detection.

Methods and apparatus for attachment to surfaces and alignment of molecules, such as nucleic acids, oligonucleotide probes and/or nano-barcodes are known in the art. (See, e.g., Bensimon et al., Phys. Rev. Lett. 74:4754-57, 1995; Michalet et al., Science 277:1518-23, 1997; U.S. Pat. Nos. 5,840,862; 6,054,327; 6,225,055; 6,248,537; 6,265,153; 6,303,296 and 6,344,319.) Nano-barcodes, coded probes and/or target molecules may be attached to a surface and aligned using physical forces inherent in an air-water meniscus or other types of interfaces. This technique is generally known as molecular combing. Nano-barcodes, coded probes and/or target molecules dissolved in an aqueous medium may be attached at either one or both ends to a surface, such as a silanized glass slide, a biotinylated surface, a gold-coated surface or any other surface known in the art capable of binding such molecules. The surface may be slowly withdrawn from the aqueous medium. Polar or charged target molecules, nano-barcodes, and/or coded probe molecules will preferentially partition into the hydrophilic (aqueous) medium. Thus, removal of the surface from the aqueous medium results in stretching of the bound target molecules, nano-barcodes and/or coded probes, parallel to the direction of movement of the meniscus. There is a direct correlation between the measured length of the stretched molecule and its actual size, with 1 pm of stretched length corresponding to about 2,000 bases of nucleic acid sequence (Herrick et al., Proc. Natl. Acad. Sci. USA 97:222-227, 2000).

Once the surface has been entirely removed from the aqueous medium, the attached nano-barcodes and/or coded probes are aligned in a parallel fashion that may be more easily and accurately analyzed. In certain embodiments of the invention where both ends of a coded probe are attached to the surface, the aligned coded probes will be arranged in a U-shaped conformation that is also more easily analyzed. The technique is not limited by the size of the target molecules, nano-barcodes and/or coded probes to be aligned, and can work on nucleic acids as long as whole chromosomes (e.g., Michalet et al., 1997; Herrick et al., 2000). At appropriate rates of movement of the meniscus the shear forces generated are relatively low, resulting in aligned DNA fragments of several hundred kilobases or longer (Michalet et al., 1997).

Molecular combing is inhibited by strong nonspecific adsorption of molecules to the treated surface (Bensimon et al., 1995). Thus, in various embodiments of the invention, the surface is treated so that only one or more ends of a target molecule or coded probe will bind to the surface. Methods for binding nucleic acids and other types of coded probes to surfaces are well known in the art and are summarized below. In a non-limiting example, target molecules, nano-barcodes or coded probes may be covalently modified with biotin residues at one or both ends of the molecule. Upon exposure to an avidin or streptavidin coated surface, only the biotinylated ends will bind to the surface. Nonspecific adsorption to a surface may be decreased by the use of surfaces that are hydrophobic in nature, such as silanized surfaces.

The embodiments of the invention are not limited by the type of surface that may be used. Non-limiting examples of surfaces include glass, functionalized glass, ceramic, plastic, polystyrene, polypropylene, polyethylene, polycarbonate, PTFE (polytetrafluoroethylene), PVP (polyvinylpyrrolidone), germanium, silicon, quartz, gallium arsenide, gold, silver, nylon, nitrocellulose or any other material known in the art that is capable of having target molecules, nano-barcodes and/or coded probes attached to the surface. Attachment may be either by covalent or noncovalent interaction. Although in certain embodiments of the invention the surface is in the form of a glass slide or cover slip, the shape of the surface is not limiting and the surface may be in any shape. In some embodiments of the invention, the surface is planar.

Alternative methods for aligning target molecules, nano-barcodes and/or coded probes on surfaces are known in the art. (E.g., Bensimon et al., 1995; Michalet et al., 1997; U.S. Pat. Nos. 5,840,862; 6,054,327; 6,225,055; 6,248,537; 6,265,153; 6,303,296 and 6,344,319). It is contemplated that any known method of alignment may be used within the scope of the claimed subject matter. In certain embodiments of the invention, alignment occurs when target molecules, nano-barcodes or coded probes dissolved in an aqueous medium are drawn through a moving meniscus. The mechanism by which the meniscus is moved is not important and may be accomplished, for example, by immersing a surface in buffer solution and slowly withdrawing it from the solution. Alternatively, a surface may be immersed in a solution and the level of the meniscus may be slowly lowered by evaporation or by removal of liquid. In another alternative embodiment of the invention, a drop of solution may be placed between a cover slip and a surface, such as a glass slide. The surface may be slowly pulled away from the cover slip. Because the solution adheres to the cover slip, this results in the formation of an air-water interface at the edge where the cover slip contacts the surface. Moving this interface aligns the target molecules, nano-barcodes and/or coded probes on the surface. Another alternative method for aligning nano-barcodes and/or coded probes, discussed in more detail below, involves use of free-flow electrophoresis either in place of or during molecular combing. Alternatively, coded probes and/or nano-barcodes may be aligned by microfluidic molecular combing, as discussed in the Examples below.

Nucleic Acids

Nucleic acid molecules to be detected, identified and/or sequenced may be prepared by any technique known in the art. In certain embodiments of the invention, the nucleic acids are naturally occurring DNA or RNA molecules. Virtually any naturally occurring nucleic acid may be detected, identified and/or sequenced by the disclosed methods including, without limit, chromosomal, mitochondrial and chloroplast DNA and ribosomal, transfer, heterogeneous nuclear and messenger RNA. In some embodiments, the nucleic acids to be analyzed may be present in crude homogenates or extracts of cells, tissues or organs. In other embodiments, the nucleic acids may be partially or fully purified before analysis. In alternative embodiments, the nucleic acid molecules to be analyzed may be prepared by chemical synthesis or by a wide variety of nucleic acid amplification, replication and/or synthetic methods known in the art.

Methods for purifying various forms of cellular nucleic acids are known. (See, e.g., *Guide to Molecular Cloning Techniques*, eds. Berger and Kimmel, Academic Press, New York, N.Y., 1987; *Molecular Cloning: A Laboratory Manual*, 2nd Ed., eds. Sambrook, Fritsch and Maniatis, Cold Spring Harbor Press, Cold Spring Harbor, N.Y., 1989). The methods disclosed in the cited references are exemplary only and any variation known in the art may be used. In cases where single stranded DNA (ssDNA) is to be analyzed, ssDNA may be prepared from double stranded DNA (dsDNA) by any known method. Such methods may involve heating dsDNA and allowing the strands to separate, or may alternatively involve preparation of ssDNA from dsDNA by known amplification or replication methods, such as cloning into M13. Any such known method may be used to prepare ssDNA or SSRNA.

Although certain embodiments of the invention concern analysis of naturally occurring nucleic acids, virtually any type of nucleic acid could be used. For example, nucleic acids prepared by various amplification techniques, such as polymerase chain reaction (PCR3) amplification, could be analyzed. (See U.S. Pat. Nos. 4,683,195, 4,683,202 and 4,800,159.) Nucleic acids to be analyzed may alternatively be cloned in standard vectors, such as plasmids, cosmids, BACs (bacterial artificial chromosomes) or YACs (yeast artificial chromosomes). (See, e.g., Berger and Kimmel, 1987; Sambrook et al., 1989.) Nucleic acid inserts may be isolated from vector DNA, for example, by excision with appropriate restriction endonucleases, followed by agarose gel electrophoresis. Methods for isolation of nucleic acid inserts are known in the art. The disclosed methods are not limited as to the source of the nucleic acid to be analyzed and any type of nucleic acid, including prokaryotic, bacterial, viral, eukaryotic, mammalian and/or human may be analyzed within the scope of the claimed subject matter.

In various embodiments of the invention, multiple copies of a single nucleic acid may be analyzed by coded probe hybridization, as discussed below. Preparation of single nucleic acids and formation of multiple copies, for example by various amplification and/or replication methods, are known in the art. Alternatively, a single clone, such as a BAC, YAC, plasmid, virus, or other vector that contains a single nucleic acid insert may be isolated, grown up and the insert removed and purified for analysis. Methods for cloning and obtaining purified nucleic acid inserts are well known in the art.

The skilled artisan will realize that the scope of the claimed subject matter is not limited to analysis of nucleic acids, but also concerns analysis of other types of biomolecules, including but not limited to proteins, lipids and polysaccharides. Methods for preparing and/or purifying various types of biomolecules are known in the art and any such method may be used.

Coded Probe Libraries

In certain embodiments of the invention, coded probes may comprise a library of probe molecules, each different probe attached to a distinguishable nano-barcode. Within a given library, it is possible that there may be more than one copy of a specific probe molecule. In this case, each copy of the same probe would be attached to an identical nano-barcode. The types of probes and nano-barcodes used are not limiting and any known type of probe molecule, including but not limited to oligonucleotides, nucleic acids, antibodies, antibody fragments, binding proteins, receptor proteins, peptides, lectins, substrates, inhibitors, activators, ligands, hormones, cytokines, etc. may be used. Further, any type of distinguishable nano-barcode may be used.

Oligonucleotide Libraries

In various embodiments of the invention, the coded probes may comprise oligonucleotide probes, such as oligonucleotides of defined sequence. The oligonucleotides may be attached to distinguishable nano-barcodes, hybridized to a nucleic acid to be analyzed and adjacent coded probes ligated together. After separation from the nucleic acid, the ligated coded probes may be attached to a surface and aligned, as discussed above. The aligned coded probes may then be analyzed by scanning probe microscopy (SPM). SPM analysis allows detection and identification of the nano-barcode component of coded probes and determination of the sequence of coded probes binding to the nucleic acid. That information can be used to identify the nucleic acid and/or to determine the nucleic acid sequence. The skilled artisan will realize that the claimed subject matter is not limited to SPM detection methods, and any method of analysis that can detect and identify nano-barcodes and/or coded probes aligned on a surface may be used. The skilled artisan will also realize that SPM analysis is not limited to detection and identification of oligonucleotide-based coded probes, but may be used with any type of coded probe and/or nano-barcode.

In alternative embodiments of the invention, coded probes may be detected without ligation of adjacent coded probes. The coded probes may be hybridized to multiple copies of the same target molecule. Non-hybridized coded probes may be removed and the hybridized coded probes detected. In some embodiments, coded probes may be detected while still hybridized to target molecules. Alternatively, coded probes may be detached from the target molecules, for example by heating the sample, and then detected. In such embodiments, the nano-barcode component may or may not be removed from the probe component of the coded probes before detection.

In certain embodiments of the invention, coded probes may be detected while still attached to a target molecule. Given the relatively weak strength of the binding interaction between short oligonucleotide probes and target nucleic acids, such methods may be more appropriate where, for example, coded probes have been covalently attached to the target molecule using cross-linking reagents, or where the binding interaction between probe molecule and target is stronger, as with antibody-antigen interactions.

In various embodiments of the invention, oligonucleotide type coded probes may be DNA, RNA, or any analog thereof, such as peptide nucleic acid (PNA), which can be used to identify a specific complementary sequence in a nucleic acid. In certain embodiments of the invention one or more coded probe libraries may be prepared for hybridization to one or more nucleic acid molecules. For example, a set of coded probes containing all 4096 or about 2000 non-complementary 6-mers, or all 16,384 or about 8,000 non-complementary 7-mers may be used. If non-complementary subsets of oligonucleotide coded probes are to be used, a plurality of hybridizations and sequence analyses may be carried out and the results of the analyses merged into a single data set by computational methods. For example, if a library comprising only non-complementary 6-mers were used for hybridization and sequence analysis, a second hybridization and analysis using the same target nucleic acid molecule hybridized to those coded probe sequences excluded from the first library may be performed.

In some embodiments of the invention, the coded probe library may contain all possible sequences for a given oligonucleotide length (e.g., a six-mer library would consist of 4096 coded probes). In such cases, certain coded probes will form hybrids with complementary coded probe sequences. Such hybrids, as well as unhybridized coded probes, may be separated from coded probes hybridized to the target molecule using known methods, such as high performance liquid chromatography (HPLC), gel permeation chromatography, gel electrophoresis, ultrafiltration and/or hydroxylapatite chromatography. Methods for the selection and generation of complete sets or specific subsets of oligonucleotides of all possible sequences for a given length are known. In various embodiments, coded probes of 2, 3, 4, 5, 6, 7, 8, 9, 10, 11, 12, 13, 14, 15, 16, 17, 18, 19, 20, 21, 22, 23, 24, 25 or more nucleotides in length may be used.

In certain embodiments of the invention, the coded probe libraries may comprise a random nucleic acid sequence in the middle of the coded probe attached to constant nucleic acid sequences at one or both ends. For example, a subset of 12-mer coded probes could consist of a complete set of random 8-mer sequences attached to constant 2-mers at each end. These coded probe libraries can be subdivided according to their constant portions and hybridized separately to a nucleic acid, followed by analysis using the combined data of each different coded probe library to determine the nucleic acid sequence. The skilled artisan will realize that the number of sublibraries required is a function of the number of constant bases that are attached to the random sequences. An alternative embodiment may use multiple hybridizations and analyses with a single coded probe library containing a specific constant portion attached to random oligonucleotide sequences. For any given site on a nucleic acid, it is possible that multiple coded probes of different, but overlapping sequence could bind to that site in a slightly offset manner. Thus, using multiple hybridizations and analyses with a single library, a complete sequence of the nucleic acid could be obtained by compiling the overlapping, offset coded probe sequences.

In embodiments of the invention involving oligonucleotide libraries, oligonucleotides may be prepared by any known method, such as by synthesis on an Applied Biosystems 38 1A DNA synthesizer (Foster City, Calif.) or similar instruments. Alternatively, oligonucleotides can be purchased from a variety of vendors (e.g., Proligo, Boulder, Colo.; Midland Certified Reagents, Midland, Tex.). In embodiments where oligonucleotides are chemically synthesized, the nano-barcodes may be covalently attached to one or more of the nucleotide precursors used for synthesis. Alternatively, the nano-barcode may be attached after the oligonucleotide probe has been synthesized. In other alternatives, the nano-barcode(s) may be attached concurrently with oligonucleotide synthesis.

In certain embodiments of the invention, coded probes may comprise peptide nucleic acids (PNAs). PNAs are a polyamide type of DNA analog with monomeric units for adenine (A), guanine (G), thymine (T), and cytosine (C). PNAs are commercially available from companies such as PE Biosystems (Foster City, Calif.). Alternatively, PNA synthesis may be performed with 9-fluoroenylmethoxycarbonyl (Fmoc) monomer activation and coupling using 0-(7-azabenzotriazol-1-yl)-1,1,3,3-tetramethyluronium hexafluorophosphate (HAW in the presence of a tertiary mine, N,N-diisopropylethylamine (DIEA). PNAs can be purified by reverse phase high performance liquid chromatography (RP-HPLC) and verified by matrix assisted laser desorption ionization—time of flight (MALDI-TOF) mass spectrometry analysis.

Nano-Barcodes

Each coded probe may incorporate at least one covalently or non-covalently attached nano-barcode. The nano-barcodes may be used to detect and/or identify individual coded probes. In certain embodiments of the invention each coded probe may have two or more attached nano-barcodes, the combination of which is unique to a particular coded probe. Combinations of nano-barcodes can be used to expand the number of distinguishable nano-barcodes available for specifically identifying a coded probe in a library. In other embodiments of the invention, the coded probes may each have a single unique nano-barcode attached. The only requirement is that the signal detected from each coded probe must be capable of distinguishably identifying that coded probe from different coded probes.

In certain embodiments of the invention, a nano-barcode may be incorporated into a precursor prior to the synthesis of a coded probe. For oligonucleotide-based coded probes, internal amino-modifications for covalent attachment at adenine (A) and guanine (G) positions are contemplated. Internal attachment may also be performed at a thymine (T) position using a commercially available phosphoramidite. In some embodiments library segments with a propylamine linker at the A and G positions may be used to attach nano-barcodes to coded probes. The introduction of an internal aminoalkyl tail allows post-synthetic attachment of the nano-barcode. Linkers may be purchased from vendors such as Synthetic Genetics (San Diego, Calif.). In one embodiment of the invention, automatic coupling using the appropriate phosphoramidite derivative of the nano-barcode is also contemplated. Such nano-barcodes may be coupled to the 5'-terminus during oligonucleotide synthesis.

In general, nano-barcodes will be covalently attached to the probe in such a manner as to minimize steric hindrance with the nano-barcodes, in order to facilitate coded probe binding to a target molecule, such as hybridization to a nucleic acid. Linkers may be used that provide a degree of flexibility to the coded probe. Homo- or hetero-bifunctional linkers are available from various commercial sources.

The point of attachment to an oligonucleotide base will vary with the base. While attachment at any position is possible, in certain embodiments attachment occurs at positions not involved in hydrogen bonding to the complementary base. Thus, for example, attachment can be to the 5 or 6 positions of pyrimidines such as uridine, cytosine and thymine. For purines such as adenine and guanine, the linkage is may be via the 8 position. The claimed methods and compositions are not limited to any particular type of probe molecule, such as oligonucleotides. Methods for attachment of nano-barcodes to other types of probes, such as peptide, protein and/or antibody probes, are known in the art.

The embodiments of the invention are not limiting as to the type of nano-barcode that may be used. It is contemplated that any type of nano-barcode known in the art may be used. Non-limiting examples include carbon nanotubes, fullerenes and submicrometer metallic barcodes.

Metallic Barcodes

Examples of submicrometer metallic barcodes of potential use as nano-barcodes are known in the art (e.g., Nicewarner-Pena et al., Science 294:137-141, 2001). Nicewarner-Pena et al. (2001) disclose methods of preparing multimetal microrods encoded with submicrometer stripes, comprised of different types of metal. This system allows for the production of a very large number of distinguishable nanbarcodes— up to 4160 using two types of metal and as many as 8×10⁵ with three different types of metal. Such nano-barcodes may be incorporated into coded probes and read by SPM technology. Methods of attaching metal particles, such as gold or silver, to oligonucleotide and other types of probe molecules are known in the art (e.g., U.S. Pat. No. 5,472,881). Metallic nanobarcodesw may be obtained from commercial sources (e.g., Nanoplex Technologies, Mountain View, Calif.).

Quantum Dot Microbeads

Nano-barcodes may also comprise quantum dot tagged microbeads, as disclosed in Han et al. (*Nature Biotech.* 19:631-635, 2001). Multicolor optical coded microbeads were created by embedding different sized quantum dots (zin-sulfide-capped cadmium selenide nanocrystals) into polymeric microbeads at precisely controlled rations. Although the 2001 publication concerned use of microbeads for fluorescent tagging and detection, the skilled artisan will realize that such beads could also be used in other detection modalities, such as SPM imaging. Alternatively, porous silicon photonic crystals, encoded through galvanostatic anodic etching, have been proposed (Cunin et al., *Nature Materials* 1:39-41, 2002). Such micron sized, nanostructured particles may also be of use for SPM detection of nano-barcodes.

Carbon Nanotubes

Another exemplary nano-barcode of use in the disclosed methods comprises single-walled carbon nanotubes (SWNTs). Nanotubes may be made in a variety of shapes and sizes that may be distinguished by SPM methods. (See, e.g., Freitag et al., Phys. Rev. B 62:R2307-R2310, 2000; Clauss et al., Europhys. Lett. 47:601-607, 1999; Clauss et al., Phys. Rev. B. 58:R4266-4269, 1998; Odom et al., Ann. N.Y. Acad. Sci. 960:203-215, 2002). Odom et al. (2002) disclose an STM (scanning tunneling microscope) technique that is capable of detecting discrete peaks in the tunneling spectra of SWNTs of 10 nm or less in size. Such peaks may represent van Hove singularities in the density of electronic states (DOS) of the carbon nanotubes.

The electronic properties of carbon nanotubes are modulated by the length of the tube. The sensitivity of the electronic wavefunction to length is illustrated by an estimate for the energy level splitting of a tube of length L.

$$-E = h v F / 2L \qquad (Eq. 1)$$

Where h is Planck's constant and vF is the Fermi velocity ($8.1 \times 10^5$ d s e c) (Venema et al., "Imaging Electron Wave Functions of Carbon Nanotubes," Los Alamos Physics Preprints:cond-mat/9811317, 23 Nov. 1996.) The difference between electron energy levels is inversely proportional to the length of the nanotube, with finer splitting observed for longer tubes.

For certain embodiments of the invention, nanotubes to be used as nano-barcodes may have tube lengths of about 10 to 200 nm and a diameter of about 1.2 to 1.4 nm. The length or diameter of the nanotubes to be used as nano-barcodes is not limited and nanotubes of virtually any length or diameter are contemplated.

It is contemplated that nanotubes may be prepared by known methods or obtained from commercial sources, for example, CarboLex (Lexington, Ky.), NanoLab (Watertown, Mass.), Materials and Electrochemical Research (Tucson, Ariz.) or Carbon Nano Technologies Inc. (Houston, Tex.). Some processing of either synthesized or purchased nanotubes may be appropriate before use. Processing may include purification of nanotubes from other contaminants, separation of nanotubes of mixed diameter and/or length into nanotubes of discrete diameter and length, removal of nanotube end caps and/or covalent modification to facilitate attachment of the nanotube to a probe to form a coded probe.

In certain embodiments of the invention, carbon nanotubes of varying length and/or diameter may be produced by a variety of techniques known in the art, including but not limited to carbon-arc discharge, chemical vapor deposition via catalytic pyrolysis of hydrocarbons, plasma assisted chemical vapor deposition, laser ablation of a catalytic metal-containing graphite target, or condensed-phase electrolysis. (See, e.g., U.S. Pat. Nos. 6,258,401, 6,283,812 and 6,297,592.) In some embodiments, nanotubes may be size sorted by mass spectrometry (See, Parker et al., J. Am. Chem. Soc. 113:7499-7503, 1991). Alternatively, nanotubes may be sorted using an AFM (atomic force microscope) or STM (scanning tunneling microscope) to precisely measure the geometry of individual nanotubes before incorporating them into coded probes. Other methods of size fractionation known in the art, such as gas chromatography, time of flight mass spectrometry, ultrafiltration or equivalent techniques are contemplated. Once sorted, the carbon nanotubes may be derivatized and covalently attached to oligonucleotide probes of known sequence or any other type of probe.

The minimum incremental change in tube length possible for a carbon nanotube is the length of the carbon-carbon bond, or about 0.142 nm. With a range of tube lengths of 200 nm, this would allow for about 1400 discrete nano-barcodes. However, the method is not limited to a single nanotube per coded probe. In alternative embodiments, multiple nanotubes of different length and diameter may be attached to a single coded probe. Using combinations of nanotubes of different length, the number of possible distinguishable nano-barcodes increases exponentially. In some embodiments, a single nanotube may be attached to a single probe molecule for simplicity of analysis.

Other embodiments of the invention concern methods of producing carbon nanotubes of defined length and diameter. In a non-limiting exemplary embodiment, a chip may contain a layer of Sic of preselected thickness, overlaying a layer composed, for example, of silicon or silicon doped with catalysts (e.g. metal atoms such as nickel). Using standard chip processing methods, such as photolithography and etching or laser ablation, the Sic layer may be divided into Sic deposits of any length, width, thickness and shape. Subsequently the chip may be heated under a vacuum, for example at about $10^{-7}$ Torr at about 1400° C., or alternatively from about $10^{-3}$ to $10^{-12}$ Torr, $10^{-4}$ to $10^{-10}$ Torr, or $10^{-5}$ to $10^{-9}$ Torr, and from 1200 to 2200° C. or 1400 to 2000° C. Under these conditions, Sic crystals spontaneously decompose and lose silicon atoms (U.S. Pat. No. 6,303,094). The remaining carbon atoms spontaneously assemble into carbon nanotubes. The size and shape of the Sic deposits may be precisely controlled to produce carbon nanotubes of any length and diameter.

The exemplary embodiments of the invention discussed above are not limiting and any method of producing carbon nanotubes of selected length and diameter may be used (e.g., U.S. Pat. Nos. 6,258,401; 6,283,812 and 6,297,592). In some embodiments, nanotube length may be adjusted by using a laser beam, electron beam, ion beam or gas plasma beam to trim the ends. Alternatively, the ends of the nanotubes could be brought into contact with a hot blade in an oxygen-containing atmosphere to oxidatively remove the ends of the tubes. A block containing the nanotubes could also be sectioned or polished to truncate the nanotubes.

In certain embodiments of the invention, carbon nanotubes may be derivatized with reactive groups to facilitate attachment to probe molecules. In a non-limiting example, nanotubes may be derivatized to contain carboxylic acid groups (U.S. Pat. No. 6,187,823). Carboxylate derivatized nanotubes may be attached to probe molecules by standard chemistries, for example by carbodiimide mediated formation of an amide linkage with a primary or secondary amine group located on the probe. The methods of derivatization and cross-linking are not limiting and any reactive group or cross-linking methods known in the art may be used.

Fullerenes

In alternative embodiments of the invention, fullerenes may be used to as nano-barcodes. Methods of producing fullerenes are well known (e.g., U.S. Pat. No. 6,358,375). Fullerenes may be derivatized and attached to probe molecules by methods similar to those disclosed above for carbon nanotubes. Fullerene-containing coded probes may be identified by SPM technologies, similar to those disclosed above for nanotubes.

In certain embodiments of the invention, fullerenes may be attached to individual nucleotides in an oligonucleotide coded probe. In such case, only two different types of distinguishable fullerenes are required, as there are only four types of nucleotide found in an oligonucleotide and two types of fullerenes may be combined in four different combinations (e.g., AA, BB, AB and BA). Where individual nucleotides are attached to nano-barcodes, it may be appropriate to use known linking groups between the nucleotide and the fullerene to avoid steric hindrance with hybridization to target nucleic acids.

The skilled artisan will realize that nano-barcodes of use in the disclosed methods are not limited to the embodiments disclosed herein, but may include any other type of known nano-barcode that may be attached to a probe and detected. Other non-limiting examples of nano-barcodes of potential use include quantum dots (e.g., Schoenfeld, et al., Proc. 7th Int. Conf. on Modulated Semiconductor Structures, Madrid, pp. 605-608, 1995; Zhao, et al., 1 st Int. Conf. on Low Dimensional Structures and Devices, Singapore, pp. 467-471, 1995). Quantum dots and other types of nano-barcodes may be synthesized by known methods and/or obtained from commercial sources (e.g., Quantum Dot Corp., Hayward, Calif.). Other nano-barcodes of potential use include nanoparticles, available, for example, from Nanoprobes Inc. (Yaphank, N.Y.) and Polysciences, Inc. (Warrington, Pa.).

Hybridization and Ligation of Oligonucleotide-Based Coded Probes

In various embodiments of the invention, hybridization of a target nucleic acid to an oligonucleotide-based coded probe library may occur under stringent conditions that only allow hybridization between fully complementary nucleic acid sequences. Low stringency hybridization is generally performed at 0.15 M to 0.9 M NaCl at a temperature range of 20° C. to 50° C. High stringency hybridization is generally performed at 0.02 M to 0.15 M NaCl at a temperature range of 50° C. to 70° C. It is understood that the temperature and/or ionic strength of an appropriate stringency are determined in part by the length of an oligonucleotide probe, the base content of the target sequences, and the presence of formamide, tetramethylammonium chloride or other solvents in the hybridization mixture. The ranges mentioned above are exemplary and the appropriate stringency for a particular hybridization reaction is often determined empirically by comparison to positive and/or negative controls. The person of ordinary skill in the art is able to routinely adjust hybridization conditions to allow for only stringent hybridization between exactly complementary nucleic acid sequences to occur.

Once short coded probes have been hybridized to a nucleic acid, adjacent coded probes may be ligated together using known methods (see, e.g., U.S. Pat. Nos. 6,013,456). Oligonucleotide sequences of as short as 6 to 8 bases may be efficiently hybridized to target nucleic acids (U.S. Pat. No. 6,013,456). Primer independent ligation may be accomplished using oligonucleotides of at least 6 to 8 bases in length (Kaczorowski and Szybalski, Gene 179:189-193, 1996; Kotler et al., Proc. Natl. Acad. Sci. USA 90:4241-45, 1993). Methods of ligating oligonucleotide coded probes that are hybridized to a nucleic acid template are known in the art (U.S. Pat. No. 6,013,456). Enzymatic ligation of adjacent oligonucleotide coded probes may utilize a DNA ligase, such as T4, T7 or Taq ligase or *E. coli* DNA ligase. Methods of enzymatic ligation are known (e.g., Sambrook et al., 1989).

Immobilization of Molecules

In various embodiments of the invention, the target molecules to be analyzed may be immobilized prior to, subsequent to and/or during coded probe binding. For example, target molecule immobilization may be used to facilitate separation of bound coded probes from unbound coded probes. In certain embodiments, target molecule immobilization may also be used to separate bound coded probes from the target molecules before coded probe detection and/or identification. Although the following discussion is directed towards immobilization of nucleic acids, the skilled artisan will realize that methods of immobilizing various types of biomolecules are known in the art and may be used in the claimed methods.

Nucleic acid immobilization may be used, for example, to facilitate separation of target nucleic acids from ligated coded probes and from unhybridized coded probes or coded probes hybridized to each other. In a non-limiting example, target nucleic acids may be immobilized and allowed to hybridize to coded probes, after which hybridized adjacent coded probes are ligated together. The substrate containing bound nucleic acids is extensively washed to remove unhybridized coded probes and coded probes hybridized to other coded probes. Following washing, the hybridized and ligated coded probes may be removed from the immobilized target nucleic acids by heating to about 90 to 95° C. for several minutes. The ligated coded probes may be attached to a surface and aligned by molecular combing, as disclosed above. The aligned coded probes may then be analyzed by SPM.

Immobilization of nucleic acids may be achieved by a variety of methods known in the art. In an exemplary embodiment of the invention, immobilization may be achieved by coating a substrate with streptavidin or avidin and the subsequent attachment of a biotinylated nucleic acid (Holmstrom et al., Anal. Biochem. 209:278-283, 1993). Immobilization may also occur by coating a silicon, glass or other substrate with poly-L-Lys (lysine), followed by covalent attachment of either amino- or sulfhydryl-modified nucleic acids using bifunctional crosslinking reagents (Running et al., *BioTechniques* 8:276-277, 1990; Newton et al., *Nucleic Acids Res.* 21:1155-62, 1993). Amine residues may be introduced onto a substrate through the use of aminosilane for cross-linking.

Immobilization may take place by direct covalent attachment of 5'-phosphorylated nucleic acids to chemically modified substrates (Rasmussen et al., *Anal. Biochem.* 198: 138-142, 1991). The covalent bond between the nucleic acid and the substrate is formed by condensation with a water-soluble carbodiimide or other cross-linking reagent. This method facilitates a predominantly 5'-attachment of the nucleic acids via their 5'-phosphates. Exemplary modified substrates would include a glass slide or cover slip that has been treated in an acid bath, exposing SiOH groups on the glass (U.S. Pat. No. 5,840,862).

DNA is commonly bound to glass by first silanizing the glass substrate, then activating with carbodiimide or glutaraldehyde. Alternative procedures may use reagents such as 3-glycidoxypropyltrimethoxysilane (GOP), vinyl silane or aminopropyltrimethoxysilane (APTS) with DNA linked via amino linkers incorporated either at the 3' or 5' end of the molecule. DNA may be bound directly to membrane substrates using ultraviolet radiation. Other non-limiting examples of immobilization techniques for nucleic acids are disclosed in U.S. Pat. Nos. 5,610,287, 5,776,674 and 6,225,068. Commercially available substrates for nucleic acid binding are available, such as Covalink, Costar, Estapor, Bangs and Dynal. The skilled artisan will realize that the disclosed methods are not limited to immobilization of nucleic acids and are also of potential use, for example, to attach one or both ends of oligonucleotide coded probes to a substrate.

The type of substrate to be used for immobilization of the nucleic acid or other target molecule is not limiting. In various embodiments of the invention, the immobilization substrate may be magnetic beads, non-magnetic beads, a planar substrate or any other conformation of solid substrate comprising almost any material. Non-limiting examples of substrates that may be used include glass, silica, silicate, PDMS (poly dimethyl siloxane), silver or other metal coated substrates, nitrocellulose, nylon, activated quartz, activated glass, polyvinylidene difluoride (PVDF), polystyrene, polyacrylamide, other polymers such as poly(vinyl chloride) or poly(methyl methacrylate), and photopolymers which contain photoreactive species such as nitrenes, carbenes and ketyl radicals capable of forming covalent links with nucleic acid molecules (See U.S. Pat. Nos. 5,405,766 and 5,986,076).

Bifunctional cross-linking reagents may be of use in various embodiments of the invention. The bifunctional cross-linking reagents can be divided according to the specificity of their functional groups, e.g., amino, guanidino, indole, or carboxyl specific groups. Of these, reagents directed to free amino groups are popular because of their commercial availability, ease of synthesis and the mild reaction conditions under which they can be applied. Exemplary methods for cross-linking molecules are disclosed in U.S. Pat. Nos. 5,603,872 and 5,401,511. Cross-linking reagents include glutaraldehyde (GAD), bifunctional oxirane (OXR), ethylene glycol diglycidyl ether (EGDE), and carbodiimides, such as 1-ethyl-3-(3-dimethylaminopropyl) carbodiimide (EDC).

Scanning Probe Microscopy

Scanning probe microscopes (SPM) are a family of instruments that are used to measure the physical properties of objects on a micrometer and/or nanometer scale. Different modalities of SPM technology are available, discussed in more detail below. Any modality of SPM analysis may be used for coded probe detection and/or identification. In general, an SPM instrument uses a very small, pointed probe in very close proximity to a surface to measure the properties of objects. In some types of SPM instruments, the probe may be mounted on a cantilever that may be a few hundred microns in length and between about 0.5 and 5.0 microns thick. Typically, the probe tip is raster-scanned across a surface in an xy pattern to map localized variations in surface properties. SPM methods of use for imaging biomolecules and/or detecting molecules of use as nano-barcodes are known in the art (e.g., Wang et al., Amer. Chem. Soc. Lett., 12:1697-98. 1996; Kim et al., Appl. Surface Sci. 130, 230, 340-132:602-609, 1998; Kobayashi et al., Appl. Surface Sci. 157:228-32, 2000; Hirahara et al., Phys. Rev. Lett. 85:5384-87, 2000; Klein et al., Applied Phys. Lett. 78:2396-98, 2001; Huang et al., Science 291:630-33, 2001; Ando et al., Proc. Natl. Acad. Sci. USA 12468-72, 2001).

Scanning Tunneling Microscopy (STM)

Scanning tunneling microscopy was the first SPM technique developed in the early 1980's. STM relies on the existence of quantum mechanical electron tunneling between the probe tip and sample surface. The tip is sharpened to a single atom point and is raster scanned across the surface, maintaining a probe-surface gap distance of a few angstroms without actually contacting the surface. A small electrical voltage difference (on the order of millivolts to a few volts) is applied between the probe tip and sample and the tunneling current between tip and sample is determined. As the tip scans across the surfaces, differences in the electrical and topographic properties of the sample cause variations in the amount of tunneling current. In certain embodiments of the invention, the relative height of the tip may be controlled by piezoelectric elements with feed-back control, interfaced with a computer. The computer can monitor the current intensity in real time and move the tip up or down to maintain a relatively constant current. In different embodiments, the height of the tip and/or current intensity may be processed by the computer to develop an image of the scanned surface.

Because STM measures the electrical properties of the sample as well as the sample topography, it is capable of distinguishing between different types of conductive material, such as different types of metal in a metal barcode. STM is also capable of measuring local electron density. Because the tunneling conductance is proportional to the local density of states (DOS), STM can also be used to distinguish carbon nanotubes that vary in their electronic properties depending on the diameter and length of the nanotube. STM may be used to detect and/or identify any nano-barcodes that differ in their electrical properties.

An STM probe tip may be scanned across a surface containing aligned coded probes to detect and identify each coded probe on the surface. Ligated coded probes may also be identified. Target molecules may be identified by determining which coded probes bind to the target molecule. In embodiments of the invention where the coded probes indicate the presence of specific sequences (such as oligonucleotide sequences), the sequence of the biomolecule may be determined from the sequence of the coded probes that bind to the target molecule.

Atomic Force Microscopy

Another modality of SPM is atomic force microscopy (AFM). Methods of biomolecule analysis by AFM are generally known in the art (e.g., Uchihashi et al., "Application of Noncontact-Mode Atomic Force Microscopy to Molecular Imaging,'In AFM microscopy, the probe is attached to a spring-loaded or flexible cantilever that is in contact with the surface to be analyzed. Contact is made within the molecular force range (i.e., within the range of interaction of Vander Waal forces). Within AFM, different modes of operation are possible, including contact mode, non-contact mode and TappingMode3.

In contact mode, the atomic force between probe tip and sample surface is measured by keeping the tip-sample distance constant and measuring the deflection of the cantilever, typically by reflecting a laser off the cantilever onto a position sensitive detector. Cantilever deflection results in a change in position of the reflected laser beam. As in STM, the height of the probe tip may be computer controlled using piezoelectric elements with feedback control. In some embodiments of the invention a relatively constant degree of deflection is maintained by raising or lowering the probe tip. Because the probe tip may be in actual (Van der Waal) contact with the sample, contact mode AFM tends to deform non-rigid samples. In non-contact mode, the tip is maintained between about 50 to 150 angstrom above the sample surface and the tip is oscillated. Van der Waals interactions between the tip and sample surface are reflected in changes in the phase, amplitude or frequency of tip oscillation. The resolution achieved in non-contact mode is relatively low.

In TappingMode3, the cantilever is oscillated at or near its resonant frequency using piezoelectric elements. The AFM tip periodically contacts (taps) the sample surface, at a frequency of about 50,000 to 500,000 cycles per second in air and a lower frequency in liquids. As the tip begins to contact the sample surface, the amplitude of the oscillation decreases. Changes in amplitude are used to determine topographic properties of the sample. Because AFM analysis does not depend on electrical conductance, it may be used to analyze the topological properties of non-conductive materials. Certain types of nano-barcodes, including but not limited to carbon nanotubes, fullerenes and nanoparticles, that differ in their topological properties may be detected and/or identified by AFM techniques.

In alternative modes of AFM, additional information may be obtained besides the topological profile of the sample. For example, in lateral force microscopy (LFM), the probe is scanned perpendicular to its length and the degree of torsion of the cantilever is determined. Cantilever torsion will be dependent on the frictional characteristics of the surface. Since the frictional characteristics of coded probes may vary depending on their composition, LFM may be useful to detect and identify different coded probes.

Another variation is chemical force microscopy (CFM), in which the probe tip is functionalized with a chemical species and scanned over a sample to detect adhesion forces between the chemical species and the sample (e.g., Frisbie et al., *Science* 265:20712074, 1994). Chemicals with differing affinities for nano-barcode materials, such as gold or silver, may be incorporated into an AFM probe tip and scanned across a surface to detect and identify nano-barcodes. Another SPM mode of potential use is force modulation imaging (Maivald et al., Nanotechnology 2:103, 1991). Uchihashi et al disclose a method of biomolecule imaging using frequency modulation in non-contact mode AFM.

Other SPM modes that may potentially be used to detect and/or identify coded probes include magnetic force microscopy (MFM), high frequency MFM, magnetoresistive sensitivity mapping (MSM), electric force microscopy (EFM), scanning capacitance microscopy (SCM), scanning spreading resistance microscopy (SSRM), tunneling AFM and conductive AFM. In certain of these modalities, magnetic properties of a sample may be determined. The skilled artisan will realize that metal barcodes and other types of nano-barcodes may be designed that are identifiable by their magnetic as well as by electrical properties.

SPM instruments of use for coded probe detection and/or identification are commercially available (e.g. Veeco Instruments, Inc., Plainview, N.Y.; Digital Instruments, Oakland, Calif.). Alternatively, custom designed SPM instruments may be used.

Nano-Barcodes and Scanning Probe Microscopy

Exemplary embodiments of the invention are illustrated in FIG. 1 through FIG. 4. FIG. 1A and FIG. 1B illustrate a non-limiting method for aligning coded probes 130 on a surface 100. A surface 100, for example a glass microscope slide 100 that has been coated with streptavidin by known methods, is immersed in a solution 110 containing, for example, biotinylated coded probes 130. The solution 110 may be contained in a container 120.

In a non-limiting example, the coded probes 130 comprise oligonucleotide probes that have been hybridized to a target nucleic acid molecule. The nucleic acid molecule may be immobilized by attachment to a nylon membrane, 96-well microtiter plate or other immobilization substrate. Biotinylated oligonucleotides comprising, for example, all 4096 possible 6-mer sequences may be obtained from commercial sources (e.g., Midland Certified Reagents, Midland, Tex.). The biotinylated oligonucleotides may be attached, for example, to submicrometer metallic barcodes (Nicewarner-Pena et al., 2001) to form coded probes 130. The coded probes 130 are allowed to hybridize to a target nucleic acid. After hybridization, adjacent coded probes 130 are ligated together using ligase. Unhybridized coded probes 130 and coded probes 130 hybridized to each other are removed by extensive washing, leaving only coded probes 130 that are hybridized to the nucleic acid. The coded probes 130 are removed by heating the solution 110 to 95° C. for five minutes. The nucleic acid attached to the immobilization substrate is removed, leaving only ligated coded probes in solution 110.

The biotinylated coded probes 130 remaining in solution 110 attach at one end to the streptavidin coated surface 100. The surface 100 is slowly removed from the solution 110. Alternatively, liquid from the solution 110 is slowly removed from the container 120, for example by evaporation or slow pumping. As the meniscus of the air-water interface slowly moves across the surface 100, the attached coded probes 130 are aligned on the surface 100. The aligned coded probes 130 may be analyzed by AFM, STM or other scanning probe methods.

Another exemplary embodiment of the invention is illustrated in FIG. 2. A drop of solution 210 containing coded probes 230 is placed on a surface 220, such as a glass slide. In certain embodiments, the slide 220 may be treated as disclosed above to bind one or both ends of the coded probes 230. The drop 210 is sandwiched between the surface 220 and a glass cover slip 200. In various embodiments, the cover slip 200 may be held in a constant position while the surface 220 is slowly pulled away from the cover slip 200. This creates a meniscus at the edge of the cover slip 200 that serves to align the coded probes 230.

In various embodiments of the invention, the coded probes 130, 230 may be attached to a surface 100,220 at both ends rather than at one end. In this case, alignment of the coded probes 130, 230 would result in a U-shaped molecule, instead of a linearized molecule (e.g U.S. Pat. No. 5,840,862). The exemplary embodiments illustrated in FIG. 1 and FIG. 2 can also be performed by attaching both ends of the coded probes 130, 230 to the surface 100, 220 (not shown).

Figure 3:
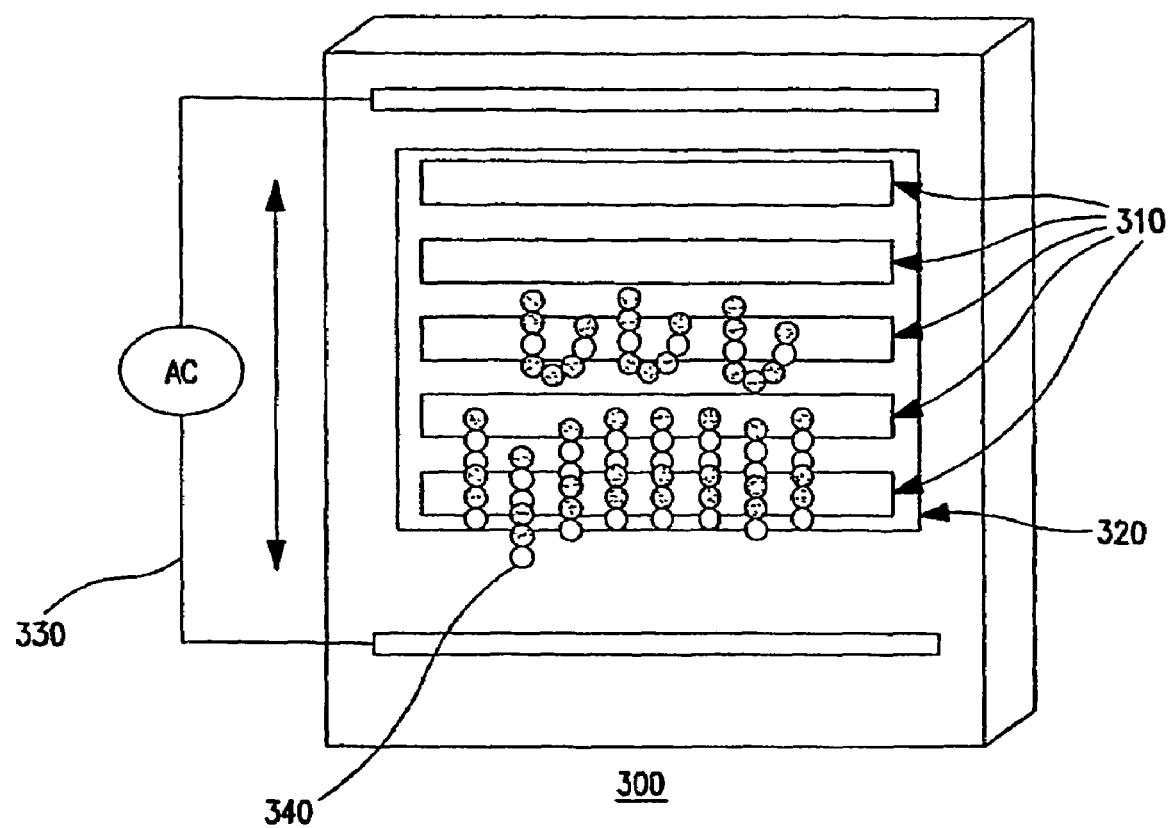
FIG. 3 illustrates another alternative exemplary method for aligning coded probes 340 on a surface 300.
Figure 4:
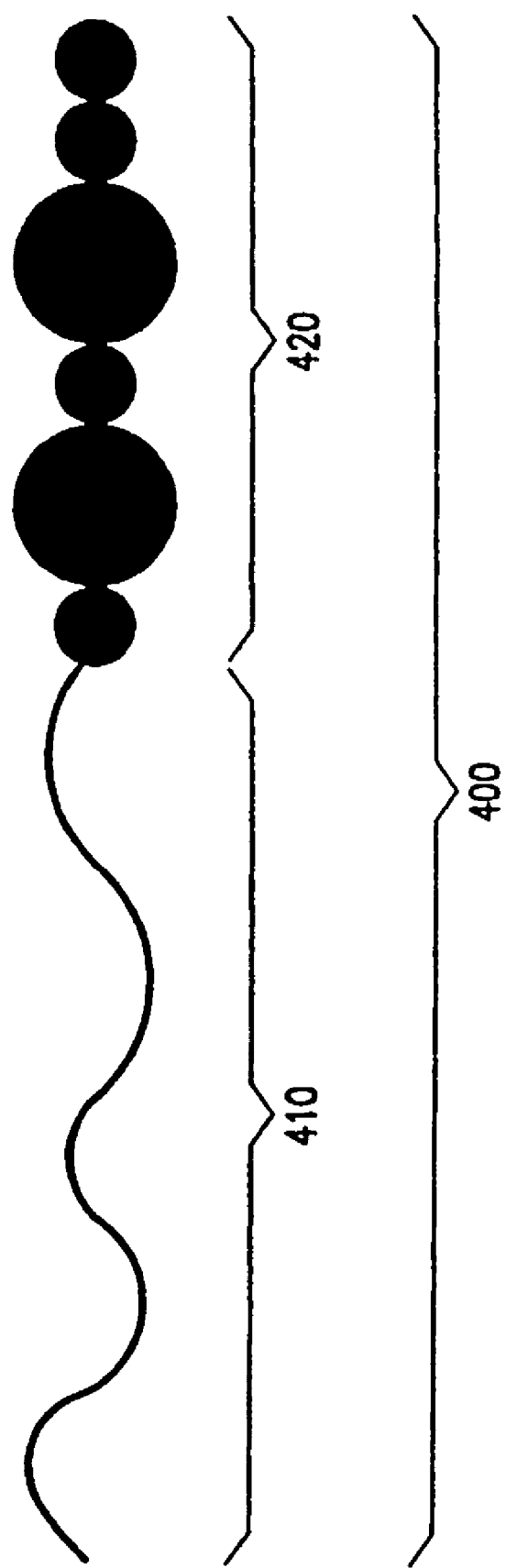
FIG. 4 illustrates an exemplary coded probe 400, comprising a nano-barcode 420 attached to a probe molecule 410. An individual nano-barcode 420 may be comprised of one or more moieties, as discussed in more detail below.

In another exemplary embodiment, illustrated in FIG. 3, coded probes 340 may be aligned on a surface 300 by free flow electrophoresis. The surface 300 may comprise alternating bands of conductive and non-conductive materials, such as strips of gold film 310 coated onto a glass sheet 320. In the presence of an alternating current electrical field 330, coded probes 340 comprising charged residues, such as the phosphate groups on oligonucleotides, will align with the field 330. Free flow electrophoresis may be used in addition to or instead of molecular combing to align coded probes 340 on a surface 300. Methods of performing free flow electrophoresis are known (e.g., Adjari and Prost, Proc. Natl. Acad. Sci. U.S.A. 88:4468-71, 1991). However, the present application presents the first use of free flow electrophoresis for aligning molecules on a surface.

EXAMPLES

Example 1

Nano-Tag Elements

Table 1 shows an exemplary list of nano-tag elements whose molecular structures may be of use for nano-barcode production. Most of the listed elements have nanometer-sized features. The nano-tag elements are grouped by parent structures and are divided into fullerene molecules, POSS (polyhedral oligomeric silsesquioxane) molecules, and organometallic compounds. POSS molecules are a relatively new type of hybrid structure, based on the silsesquioxane cage structure. Fullerene and POSS molecules are nearly symmetric three-dimensional structures, whereas the organometallic compounds are either planar or non-symmetric three-dimensional structures. Fullerenes exhibit relatively low solubility in any solvent. POSS molecules are used as additives in plastic polymers and tend to exhibit aggregation over individual deposition. Organometallic compounds have the advantage of enormous diversity, due to the combinatorial pairing of metallic centers with organic counterparts. In addition, the three-dimensional diversity of these molecules ranges from 3D asymmetric to 2D symmetric. Many of the organometallic compounds can be bi-functionalized for downstream processing of elements into barcodes. Organometallic molecules have been subjects of numerous imaging studies and have features that are readily observed by molecular imaging. The skilled artisan will realize that the nano-tag elements listed in Table 1 are exemplary only. A wide variety of nano-tag elements are known in the art and may be used to make nano-barcodes, including but not limited to quantum dots and carbon nanotubes. Any such known nano-tag element may be used to produce nano-barcodes and coded probes.

Example 2

Synthetic Schemes

Bifunctional Intermediates

FIG. 5 illustrates an exemplary scheme for nano-tag-mediated barcode synthesis, involving production of bi-functionalized nano-tag elements that are used as a building block for a controlled stepwise head-to-tail assembly of individual units into a specific polymer sequence. This approach has been used in molecular biochemistry to make peptides and oligonucleotides on automated solid phase synthesizers. FIG. 5A shows the initial conversion of an exemplary nano-tag element into a bi-functional molecule. Two functional moieties (R1 and R2) are shown attached to opposite ends of the tag element. FIG. 5B illustrates the selective and transient protection of one group with activation of the other functional group. Such techniques are well known, for example, in solid phase peptide synthesis. FIG. 5C illustrates the stepwise addition of building blocks in a controlled polymerization. Typically, the transient protecting group is removed from the terminus of the growing polymer and the next building block is coupled to the newly deprotected terminus. Multiple cycles give rise to increasing length of barcode polymer.

Exemplary R1 functional groups include $CH_2OH$ and $CONHC_3H_6NH_2$. Exemplary R2 functional groups include $CH_2OH$ and $COOH$. Where a $CH_2OH$ is used as the R1 and R2 groups, the R1 group may be protected with a dimethoxytrityl moiety, which may be removed by acid treatment. The R2 group may then be activated by cyanoethyl-N,N-diisopropyl phosphoramidite. Where the R1 group is $CONHC_3H_6NH_2$ and the R2 group is COOH, the R1 group may be protected by a trityl moiety, which may be removed by acid treatment. The R2 group may be activated, for example, by carbodiimide treatment. Other protectiodeprotection chemistries are well known, for example in solid phase peptide or oligonucleotide synthesis and any such known methods may be utilized for nano-barcode production.

Backbone Mediated Synthesis

Backbone mediated nano-barcode synthesis is modeled after standard peptide or oligonucleotide solid phase synthesis. The nano-tag element is converted into a mono-functionalized analog and then attached to either an amino acid or to a nucleotide phosphoramidite. The building blocks would be appropriately blocked and activated for standard automated solid phase synthesis. The overall scheme is illustrated in FIG. 6. The tag unit is initially monofunctionalized by addition of an appropriate R group (FIG. 6A). Using either peptide or oligonucleotide based polymerization, the functionalized tag group is converted to a covalently tagged amino acid subunit (FIG. 6B) or nucleotide subunit (FIG. 6C).

One consideration in such a scheme is the choice of backbone and the known physical and chemical properties of naturally occurring polymeric molecules, such as polypeptides and oligonucleotides. Chemical attachment of tag elements to amino acids or oligonucleotide analogs should be of equal difficulty. The phosphoramidite polymerization chemistry is 10 fold more robust than peptide chemistry, and would be more compatible with the down stream synthesis of coded probes. However, peptides can give rise to secondary structures such as the alpha helix that could provide structural entropy to the coded probes. Table 2 summarizes candidates based on commercially available starting products. The skilled artisan will realize that the listed candidate subunits are exemplary only and that a wide variety of other potential subunits are known in the art and may be utilized.

Polymer Decoration with Nano-Tag Elements

Another alternative approach to coded probe synthesis entails creating polymer scaffolds to which nano-tag elements are attached through post-polymer assembly. For example, peptides and oligonucleotides provide linear scaffold molecules to which nano-tag elements may be attached post-assembly. Advantageously, methods of peptide and oligonucleotide production are well known in the art. However, other forms of nano-structures may provide multi-dimensional scaffolds. A difficulty with this approach is that it is difficult to put more than one kind of tag element (not including spacers) into the polymer. The high specificity for protection/deprotection also limits such schemes. Steric hindrance may also prevent complete decoration. This process is the least difficult for creating exemplary of coded probes, as the polymer synthesis part of the scheme is well characterized and methods of post-translational modification of peptides and oligonucleotides are known. A non-limiting example of a coded probe based on oligonucleotides is provided in the Examples below. The branch points on the exemplary oligonucleotide based coded probe may be detected by SPM techniques, or may serve as attachment sites for nanoparticles or other types of nano-tag elements.

A peptide or oligonucleotide that has active groups at specific appropriately spaced sites may be purchased from commercial sources. The polymer may then be exposed to a mono-functionalized nano-tag element and all of the active sites would be modified. Depending on the strategy, solid phase chemistry techniques may be used for decorating with nano-tag elements, preventing unwanted intermolecular polymerization.

Table 3 lists exemplary mono-functionalized tag elements and their related polymers for decoration. All components listed are currently commercially available and the decoration chemistry is known. Complete labeling and solubility are important. As the molecules are decorated, their solubility is affected, often leading to precipitation. Also, the structures are subject to secondary and tertiary structural properties, giving rise to complex folding patterns. Folding may be affected by deposition onto a flat surface. Thus, a more rigid backbone may exhibit certain advantages. The skilled artisan will realize that the listed fimctionalized nano-tag elements are not limiting and that a variety of other functionalized nano-tag elements, such as quantum dots or carbon nanotubes, are known and may be used.

Direct Read of Polymer Subunits

A fourth strategy is based on STM imaging of charge densities of certain amino acids or nucleotide analogs. This approach could be accomplished by commercially obtaining peptide or oligonucleotide synthesis of specified sequences, followed by spotting and imaging. Table 4 lists several exemplary subunits and their incorporation into a polymer sequence. Secondary structures and imaging presentation may be considered when designing these polymers.

Exemplary coded probe subunits were and their characteristics were determined, as disclosed in the following Examples.

Example 3

Synthesis of Exemplary Coded Probe Subunits

Peptide Polymers

An exemplary peptide polymer, of potential use for production of either a decorated polymer or direct polymer imaging, was prepared (SEQ ID NO:1). A 5 mg scale solid-phase peptide synthesis was performed. The resulting peptide was HPLC purified to about 98% purity. Mass spectroscopy was used to demonstrate the presence of the full length product. The carboxyl terminal end of the peptide was modified to form an amide terminal group.

AAMAAKAMAAMAKAVAMAAKAVAAMAKAAA    (SEQ ID NO:1)

The sequence was predicted to be an alpha helix, based on sequence similarity to keratins, Rop protein and poly-alanine, with the amino terminus and the secondary amines from lysine facing the same side of the helix. These amines make excellent attachment sites for any molecule mono-functionalized with an activated carboxyl group, using standard dicyclohexylcarbodiimide (DCC) or water soluble carbodiimide cross-linking. The amide blocking group on the carboxyl terminus was used to prevent polymerization of peptides to each other.

Potential quaternary structure formation into helical bundles (e.g., 4-helix bundle) may be eliminated or minimized by decorating the lysine side chains. Peptide concentration also plays a role in affecting the formation of higher ordered structures.

A second synthetic peptide sequence (SEQ ID NO:2) was prepared by standard solid-phase peptide synthesis, as discussed above. The sequence was designed to examine the different amino acids and their imaging capacity. An alpha helix structure was designed by loading one side with helix preferring amino acids and decorating the other side with the side chains of other amino acids. Thus, alanine and methionine residues were placed on one side of the helix, while representatives of the remaining amino acids were placed on the other side of the helix.

GALYAMARAVHAMAEAACQAAWAMG    (SEQ ID NO:2)

Bi-Functional Fullerenes

An exemplary bifunctional nano-barcode subunit, compatible with solid phase oligonucleotide synthesis, was designed around the structure of a modified C70 fullerene. In certain embodiments of the invention, primary alcohols are utilized for the two functional groups, thus creating a diol-fullerene analog. Secondary and tertiary alcohols may also be used, although they are less reactive and more sterically hindered. The first part of the synthesis involves formation of the bi-functionalized fullerene molecule, where the functional groups may be OH, $CH_2OH$ or COOH. In alternative embodiments, a di-carboxylated fullerene may be prepared and the carboxyl groups reacted with a reagent such as 1-amino,3-propanol in the presence of a condensing reagent (e.g., DCC) to create two alcohols. The amine groups condense with the carboxyls, resulting in the attachment of a hydrocarbon chain terminating in a hydroxyl residue. This pathway can lead to several useful products differing in the length of the hydrocarbon chain and ultimately affecting the spacing of fullerenes upon controlled assembly of a fullerene chain. One caveat of using a carboxylated fullerene is the additional reactions involved, resulting in less product and lower yield.

Following derivitization, the bi-functionalized product(s) are purified. In order to effectively form coded probes from the bi-functionalized subunit, the two functional groups are located at opposite ends of the molecule. Impurities with one functionality or with two adjacent modifications are removed, Although location of the two functional groups at less than 180° separation may be feasible, the location of the two functional groups at less than 150° is not acceptable for coded probe formation.

Figure 7:
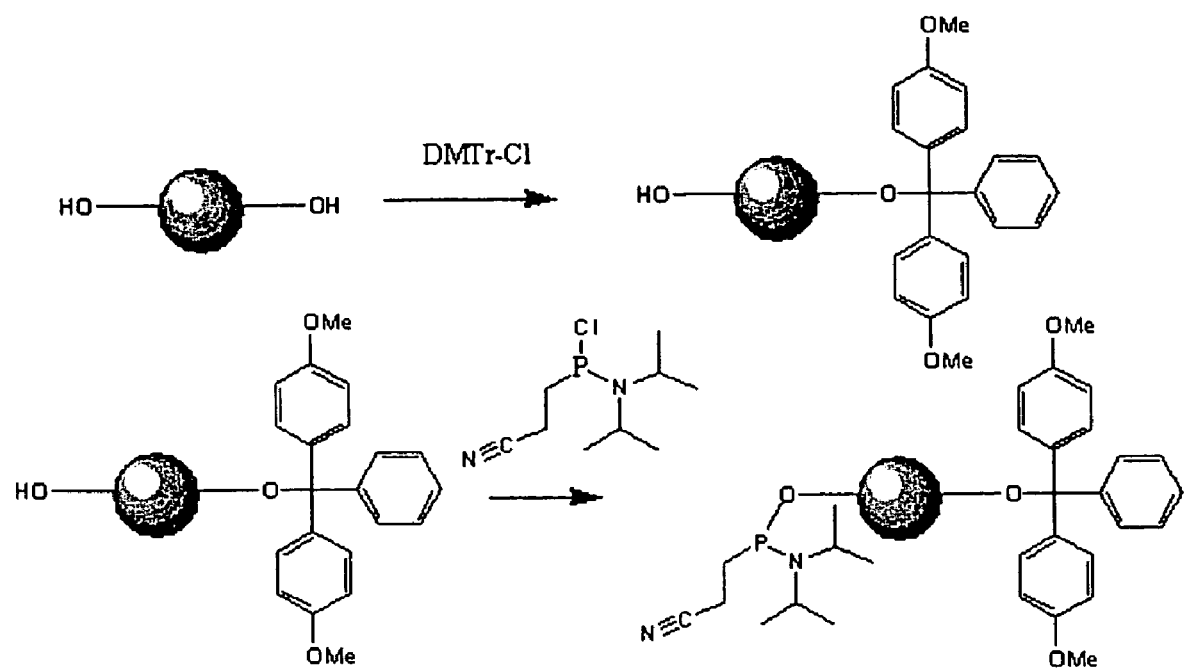
FIG. 7 shows an exemplary modification of a bi-functional fullerene diol for incorporation into a coded probe.

The purified diol product is further modified into a building block for synthesis, as disclosed in FIG. 7. The tritylation reaction is straightforward, involving the reaction of the diol modified fullerene with a dimethyl-trityl-chloride. The derivatization with DMT-Cl produces a mixture of the desired mono-DMT and bis-DMT. The mono-tritylated product is purified and separated from the di-tritylated product. Phosphoramidation of the monotritylated product occurs by a standard reaction under inert reaction conditions. The chloro-2cyanoethyl-N,Ndiisopropyl-phosphoramidite reagent is commercially available and is best used fresh and only once. The reaction proceeds immediately, giving high yield. The products formed in this reaction will give increasing mobility on silica gel chromatography, allowing simple purification. The final product is often cleaned using a small pad of silica. The final product is dried under vacuum and stored dry under argon. The product may be incorporated into a polymer sequence using standard phosphoramidite chemistry.

Taking advantage of the non-perfect spherical shape of C(70) presumably due to localized electron distributions focused on two opposite polar ends, a bi-functional C(70) subunit was designed. The C(70) fullerene was chosen to provide a scaffold with two types of most reactive bonds located at the opposite sites. Five bi-substituted isomers were expected, including two pairs of enantiomers. A design incorporating two types of hydroxyl groups, which are present in nucleosides, allows the use of common protocols for oligonucleotide synthesis. The primary alcohol is predominantly derivatized by DMT-Cl, leaving a secondary alcohol available for phosphitylation. The alcohol groups are separated from the C(70) scaffold by a $C_2$-$C_8$ linker.

Figure 8:
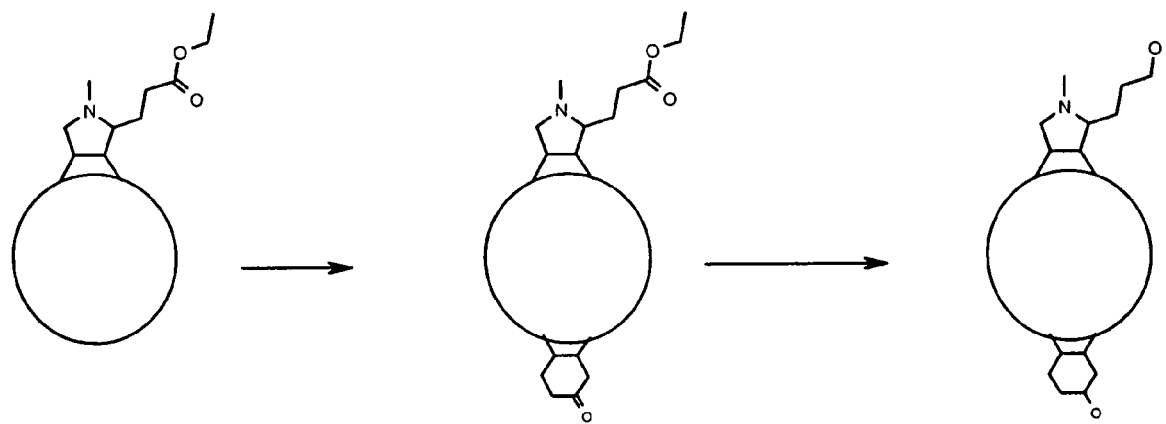
FIG. 8 shows an exemplary structure of a bi-functional fullerene of use in coded probe synthesis.

An exemplary structure of a bi-functional fullerene, containing a primary and a secondary alcohol, is illustrated in FIG. 8. To form the primary alcohol, a monocarboxylic acid moiety can be introduced by Reformatsky-type reaction using organozinc reagents or by Prato addition using, for example, succinic acid semi-aldehyde leading to a substituted pyrrolidine derivative. Expected yields are 15-30%. The C(70) ester can be reduced with Dibal-H together with the carbonyl group. The precursor of the secondary alcohol moiety, a ketone, may be introduced using the Prato addition or Diels-Alder approach, with the commercially available trimethylsilyl enol of methyl vinyl ketone. The yields are 35% and 50%.

Example 4

Production of Exemplary Bi-Functional Fullerene

In an exemplary embodiment of the invention, a C70 fullerene-diol was produced that was converted to the DMTr (dimethoxytrityl) protected and phosphoramidite activated compound. This product may be used for synthesis of nano-barcodes. The phosphate backbone created by condensation of the phosphoramidite moiety may enhance water solubility of the fullerenes, facilitating later use of the resulting coded probes.

A C70-diol intermediate of use for bifunctional fullerene synthesis was obtained from New England Peptide synthesis division (Fitchburg, Mass.). The intermediate product had limited solubility in appropriate solvents for blocking activation and polymerization. The product showed spontaneous reversion to the parent compound with a half-life estimated at ~1.0 year.

Oligonucleotide and peptide nucleic acid-based coded probes were also produced, using the schemes disclosed above, synthesized by Midland Certified Reagents (Midland, Tex.), Applied Biosystems (Foster City, Calif.) or QIAGEN Operon (Alameda, Calif.).

Example 5

Substrate Preparation and Molecule Attachment

A variety of substrates may be used for imaging of coded probes. Imaging is slow (on the order of minutes) and molecules move rapidly (fractions of seconds). Thus, in order to limit the molecular motions, samples must be absorbed onto the substrate and become part of the crystal lattice. The imaging of DNA by AFM using mica exemplifies this concept. DNA binds mica through the phosphate backbone using a divalent metal such as $Ni^{2+}$ or $Mg^{2+}$. DNA and mica are both negatively charged, and it is necessary to use a counterion such as $Mg^{2+}$ or $Ni^{2+}$ to adsorb DNA onto the mica (*Biophys. J.* 70:1933, 1996; PNAS 94:496, 1997; *Biochemistry* 36:461, 1997). The divalent cations work as a counterion on the negatively charged DNA backbone and also give additional charges to bind the mica. AP-mica (functionalized aminopropyl mica) has been used to bind DNA for AFM (*Proc. Natl. Acad. Sci. USA* 94:496, 1997).

Annealing Gold-on-Mica Substrates

A quartz capillary torch was made by pulling a piece of 1.00 mm o.d., 0.75 mm i.d. quartz capillary in a Sutter Instrumerits P-2000 capillary puller. The glass was scored and broken at a point where the capillary had an ID of about 200 μm. The surface was then lapped flat and polished using 3M imperial lapping film. Quartz discs were heated on a heating block at 130° C. for 5 minutes. The discs were flamed with a hydrogen torch using a 1.5 inch flame from the quartz tip. Fresh gold substrate was placed (butter side up) on the center of the disc using tweezers. The substrate was held down using a pre-flamed 1 cm×1 cm×1 mm quartz block which only touched the mica surface and was left to heat for 5 minutes. The quartz capillary torch was held at 30° to the plane of the disc, such that the tip of the flame just touched the gold surface. The flame was passed repetitively over the gold surface (45 times) using a two inch pass in one second cycles. The substrate was stored under argon in its original container until use.

DNA Deposition on Substrate

DNA was deposited on mica and scanned by AFM. A population of different size plasmid molecules (differing by 1,000 bases in length) ranging from 1-10 Kb was used and AFM images were obtained (not shown).

Direct Attachment to Gold

Molecules to be imaged may be attached to a substrate directly or indirectly. Direct attachment involves modifying the nano-tag with a functional group that specifically reacts with the substrate to create a covalent bond. Conditions for nucleophilic attack of sulfur on reduced gold under aqueous conditions are known in the art. This approach has been optimized and appears feasible under mild conditions. The redox kinetics for direct attachment may be controlled with pH. The reaction is specific and should not cross-react with other nano-tags. Another approach may use a more reactive attacking group, such as a radical based mechanisms or photo-catalyzed reactions. In general, radical reaction kinetics are fast and robust, but often lack control. One final approach uses a caged sulfur analog that is deprotected with light or pH. This approach would use a similar mechanism as the first approach but has an added element of specificity for initiating and localizing the reaction. Exemplary reactive moieties for covalent attachment to gold surfaces include sulfhydryl groups, oxygen radicals, carbon radicals and photoactivated reagents, such as various sulfur compounds known in the art. Of these, attachment of sulfhydryl-modified oligonucleotides to gold surfaces is the most extensively studied and has been disclosed in numerous publications. In addition, thiol-modified oligonucleotide probes are commercially available from standard sources (e.g., Midland Certified Reagents, Midland Tex.).

Indirect Attachment to Gold

Indirect attachment of targets to substrates involves a "linker" molecule to provide an attachment site to the substrate as well as to the nano-barcode. In this strategy a bi-functional linker molecule is used. The linker molecule has one functional group for attachment to gold and another for attachment to the barcode. One advantage to this approach is that a substrate can be modified with linker molecules at the desired density and verified by imaging prior to attaching the barcodes through a second reaction.

In a non-limiting example, the linker molecule may be attached to gold using a sulfhydryl group, with a different functional group at the opposite end of the linker. One non-limiting example would be a carboxyl group. Aminolated spacer barcodes can be specifically (but irreversibly) reacted with a terminal carboxyl. Carbodiimide-mediated condensation of amine with carboxyl groups is a well-understood chemical route.

Example 7

STM Imaging

Gold Nanoparticles

AFM images were obtained with gold nanoparticles and lambda DNA. The substrates used were a poly L-lysine coated glass cover slip and amino-treated mica (AP-mica). AP-mica was obtained by vapor phase treatment of freshly cleaved mica with 3-aminopropyltriethoxy silane). Gold nanoparticles of 50 nm, 10 nm, 5 nm and 2 nm were purchased from Ted-pella Inc. (Redding, Calif.). With a poly L-lysine coverslip substrate, 10 μl of gold colloidal solution was left to dry on the coverslip. With AP-mica, 100 μl of gold colloidal solution was placed on the substrate for 15 min. Excess solution was then wicked off with a Kimwipe. AFM imaging of the AP-mica substrate, using a Digital Instruments NanoScope® in tapping mode AFM, showed a smooth, featureless surface. The AP-mica proved to be a good surface for immobilizing gold nanoparticles. The 50 nm gold nanoparticles were easily imaged by AFM (not shown). The 5 and 10 nm gold nanoparticles were also clearly visible by AFM (not shown). The 2 nm gold nanoparticles were individually distinguishable, although the image resolution was not as sharp as with larger nanoparticles (not shown).

It was possible to distinguish between different sized nanoparticles in a mixture of 10, 5 and 2 nm gold nanoparticles (not shown). The 2 and 5 nm nanoparticles could be distinguished by the measured height using tapping mode AFM. These results show that nano-barcodes based upon different sized nanoparticles may be distinguished by SPM imaging techniques.

In another non-limiting example, 20 μl of poly-L-lysine solution (0.01% from Sigma Chemicals, St. Louis, Mo.) was placed onto a mica substrate for about 5 minutes, then rinsed with nanopure water (18 MΩ) and dried under filtered $N_2$ gas. Gold nanoparticles (from Polysciences or Ted-Pella Inc.) were sonicated for 30 sec. A 25 μl sample of undiluted nanoparticles was placed onto the poly-L-lysine coated mica for about 10 min, then rinsed with nanopure water and dried under filtered $N_2$ gas. Images were obtained with a Digital Instruments NanoScope® in tapping mode AFM (not shown).

Figure 9:
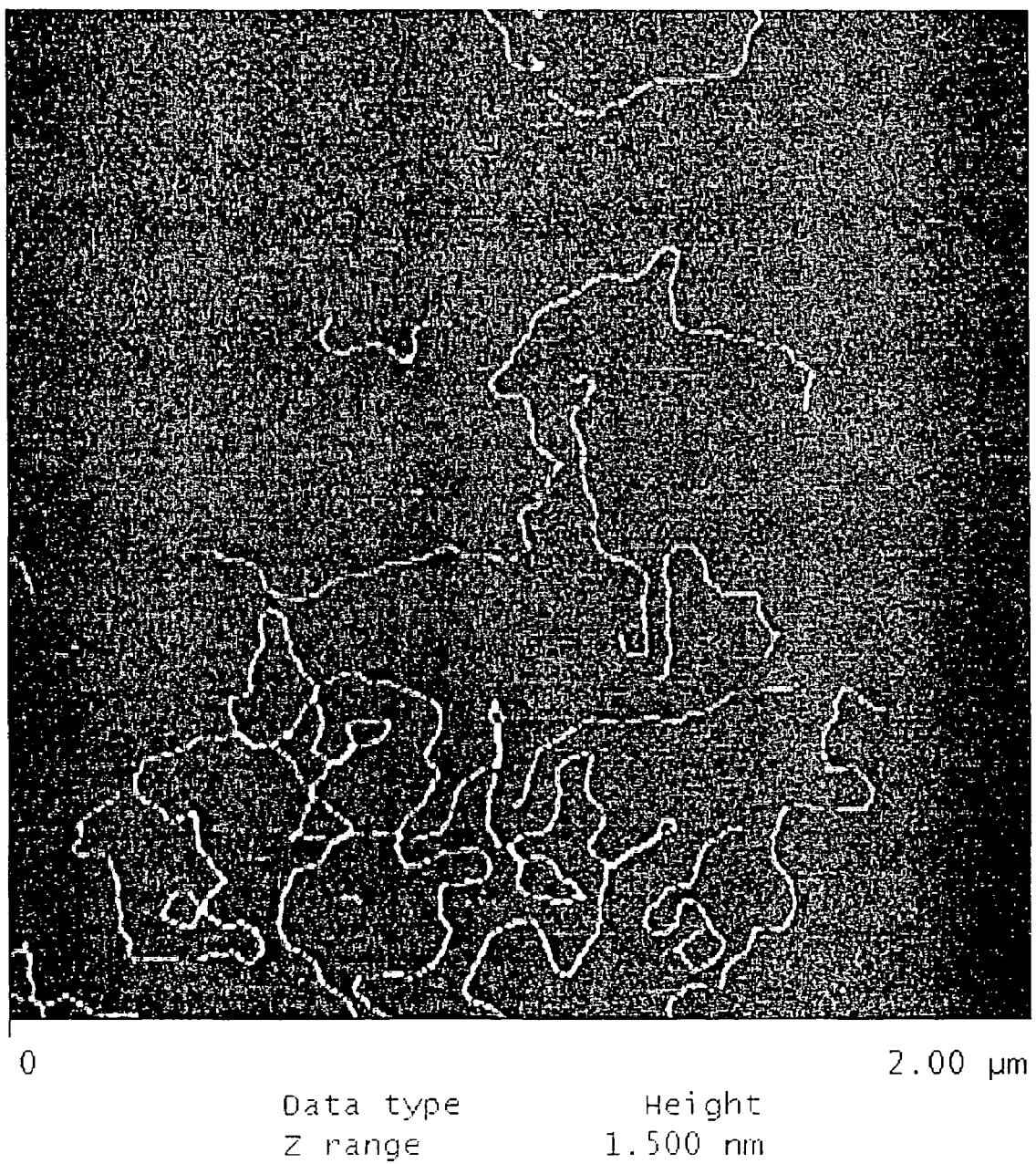
FIG. 9 shows an exemplary image of digested lambda DNA obtained by atomic force microscopy.

A Hind III digest of lambda DNA was also imaged by AFM. A 1 μg/ml solution of digested lambda DNA was prepared in HEPES buffer (40 mM HEPES, 5 mM NiCl, pH 6.8). A 30 μl sample of DNA solution was deposited onto a treated mica substrate for 10 min, rinsed with nanopure water and dried under $N_2$ gas. The AFM images of digested lambda DNA are shown in FIG. 9. The double-stranded DNA molecules are clearly visible by AFM imaging.

Fullerenes

An image of a single fullerene molecule deposited on a graphite surface was obtained by STM imaging, using a Digital Instruments NanoScope® with a 14.46 nm scan size (not shown). Multiple fullerenes were connected by peptides and imaged. Four fullerenes were attached to the peptide of SEQ ID NO: 1 and an image was obtained by STM scanning, showing each of the four fullerenes (not shown).

Example 8

Alignment of Nucleic Acids

Lambda DNA was aligned by microfluidic molecular combing. A microfluidic channel was prepared in a layer of PDMS overlaying a substrate. Microfluidic channels were made by molding polydimethylsiloxane (PDMS) according to Anderson et al. ("Fabrication of topologically complex three-dimensional microfluidic systems in PDMS by rapid prototyping," Anal. Chem. 72:3 158-3164, 2000). The substrate may comprise, for example, AP-mica or a gold coated substrate prepared as discussed above. A sample may be introduced into a chamber at one end of a microfluidic channel and a vacuum applied to a reservoir at the other end of the channel. The addition of one or more posts within the channel allows for molecule alignment by molecular combing. The PDMS layer is removed and the substrate rinsed with nanopure water and dried with $N_2$ gas. Various alignments may be formed using multiple chambers and/or microfludic channels, different patterns of microfludic components, different microfluidic streams and different structures within the channels.

Figure 10:
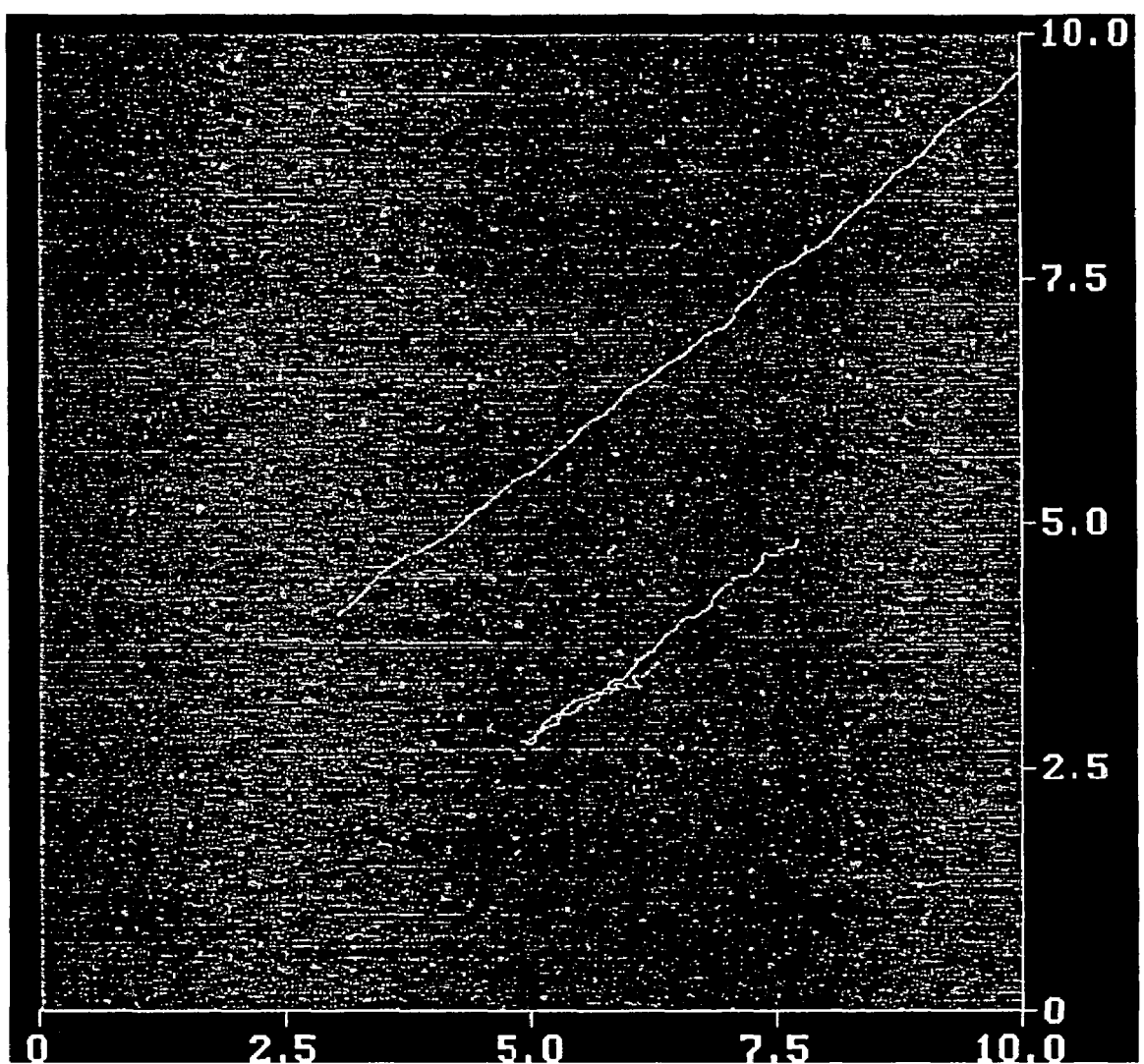
FIG. 10 shows an example of DNA molecules aligned by microfluidic molecular combing (MMC).
Figure 11:
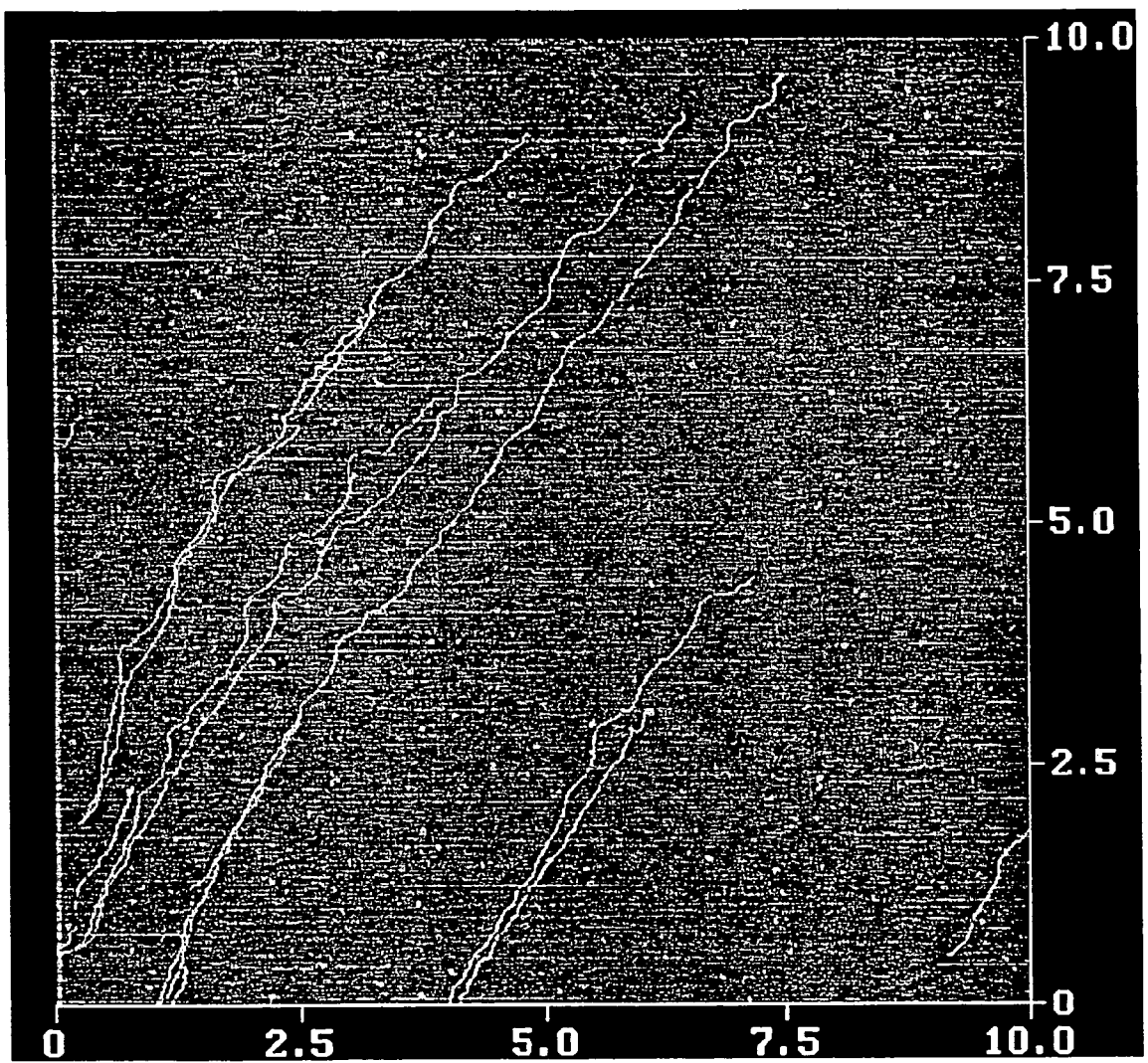
FIG. 11 shows another example of DNA molecules aligned by microfluidic molecular combing (MMC).

FIG. 10 and FIG. 11 show examples of lambda DNA molecules, aligned by the MMC process. The fully stretched and aligned lambda DNA was about 17 μm in length. Molecules were aligned parallel to the direction of microfluidic flow, as expected. This result demonstrates the feasibility of aligning coded probes on a surface, either hybridized to a target or else hybridized and then released. The alignment of the coded probe molecules facilitates their imaging and identification by SPM imaging techniques.

Example 9

AFM Imaging of Oligonucleotide Based Coded Probe

Figure 12:
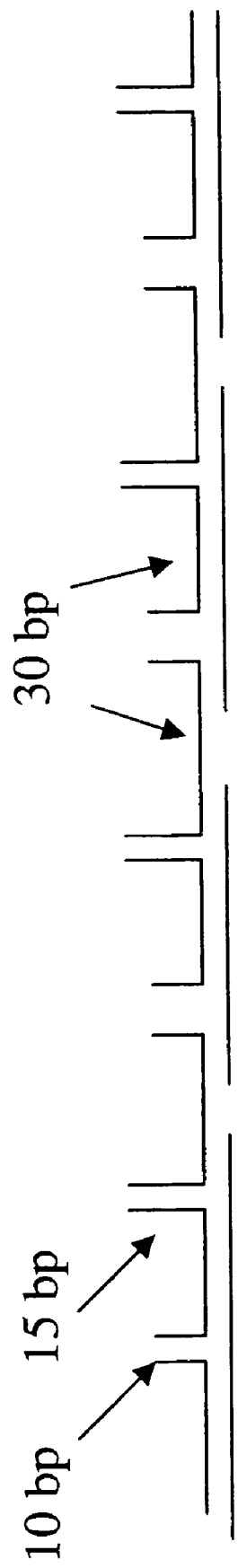
FIG. 12 illustrates an exemplary oligonucleotide based nano-barcode made up of 13 individual oligonucleotide strands hybridized together.
Figure 13:
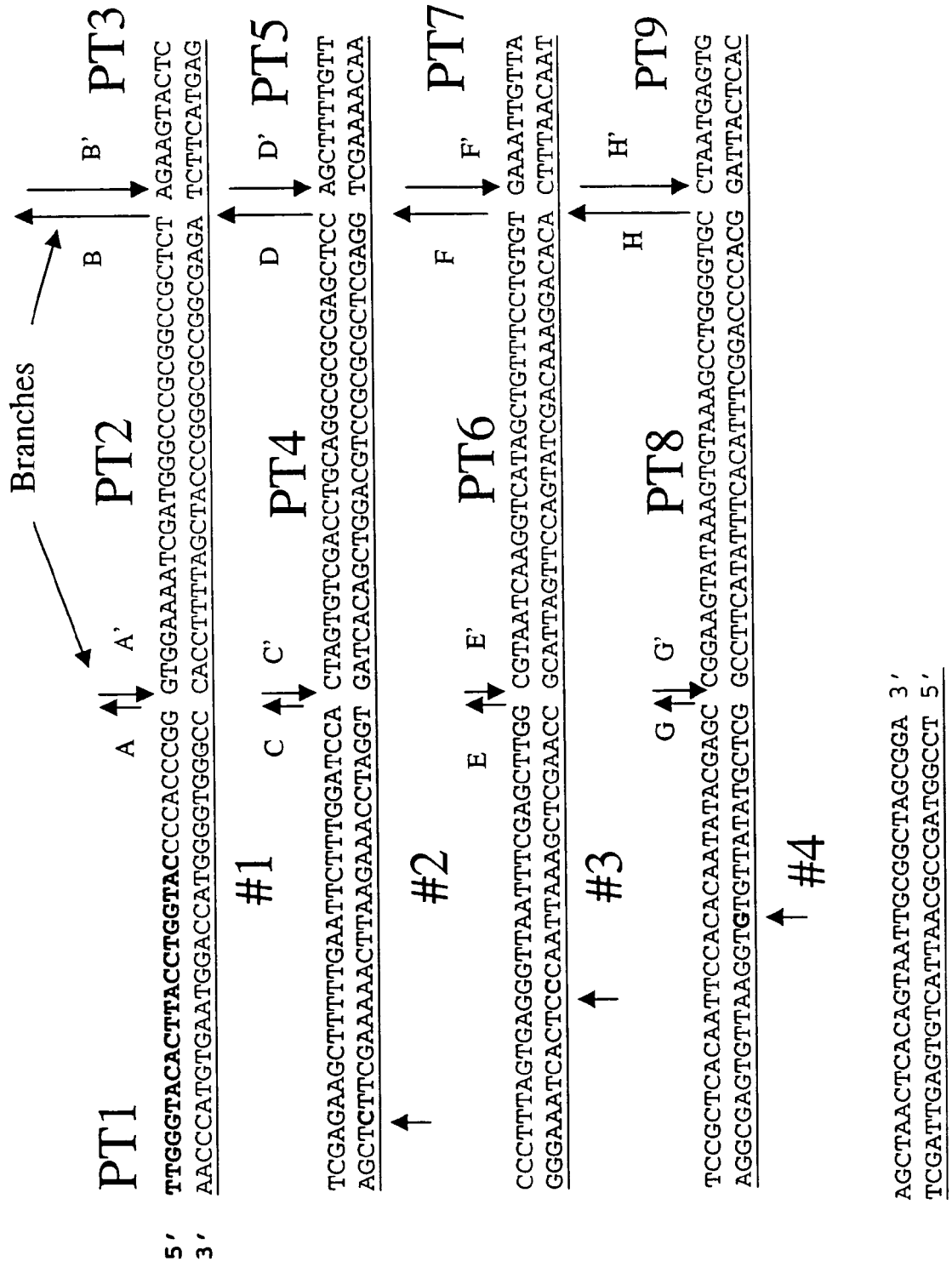
FIG. 13 shows the individual oligonucleotide components of the nano-barcode of FIG. 12. Note that, as shown in FIG. 12, there are 9 fragments (labeled PT1 to PT9, in order), which correspond to the underlined segments of sequences represented in FIG. 14 (SEQ ID NOS:3 to 11) used to make the top stand of the nano-barcode and 4 fragments (labeled #1 to #4) used to make the bottom strand (SEQ ID NOS: 12 to 15). PT1 corresponds to residue numbers 1-30 of SEQ ID NO:3. PT2 corresponds to residue numbers 11-40 of SEQ ID NO: 4. PT3 corresponds to residue numbers 21-60 of SEQ ID NO:5. PT4 corresponds to residue numbers 11-40 of SEQ ID NO:6. PT5 corresponds to residue numbers 21-60 of SEQ ID NO:7. PT6 corresponds to residue numbers 11-40 of SEQ ID NO:8. PT7 corresponds to residue numbers 21-60 of SEQ ID NO:9. PT8 corresponds to residue numbers 11-40 of SEQ ID NO:10. PT9 corresponds to residue numbers 22-61 of SEQ ID NO: 11. The hybridized nano-barcode exhibits branch points detectable by scanning probe microscopy.

In another non-limiting example, coded probes may be produced as a set of short oligonucleotide sequences hybridized together, as illustrated in FIG. 12. Each line in the Figure represents a single synthetic oligonucleotide, 9 on the top strand and 4 on the bottom strand. Hybridization creates branch points that may be imaged by SPM techniques. Alternatively, the branch points may serve as attachment sites for metal nanoparticles or other tag elements, as discussed above. An exemplary oligonucleotide coded probe sequence is provide in FIG. 13, showing the sequences of the top and bottom strands hybridized to each other. For clarity, the branch sequences are not shown in FIG. 13. FIG. 14 shows the complete sequences of the 9 separate oligonucleotides that form the top strand of the coded probe. The portions that hybridize to each other to form branch sites are indicated. For example, the 3' end of PT1 (SEQ ID NO:3), labeled "A", hybridizes to the 5' end of PT2 (SEQ ID NO:4), labeled "A." Similarly, B binds to B', C binds to C', etc.

Figure 15:
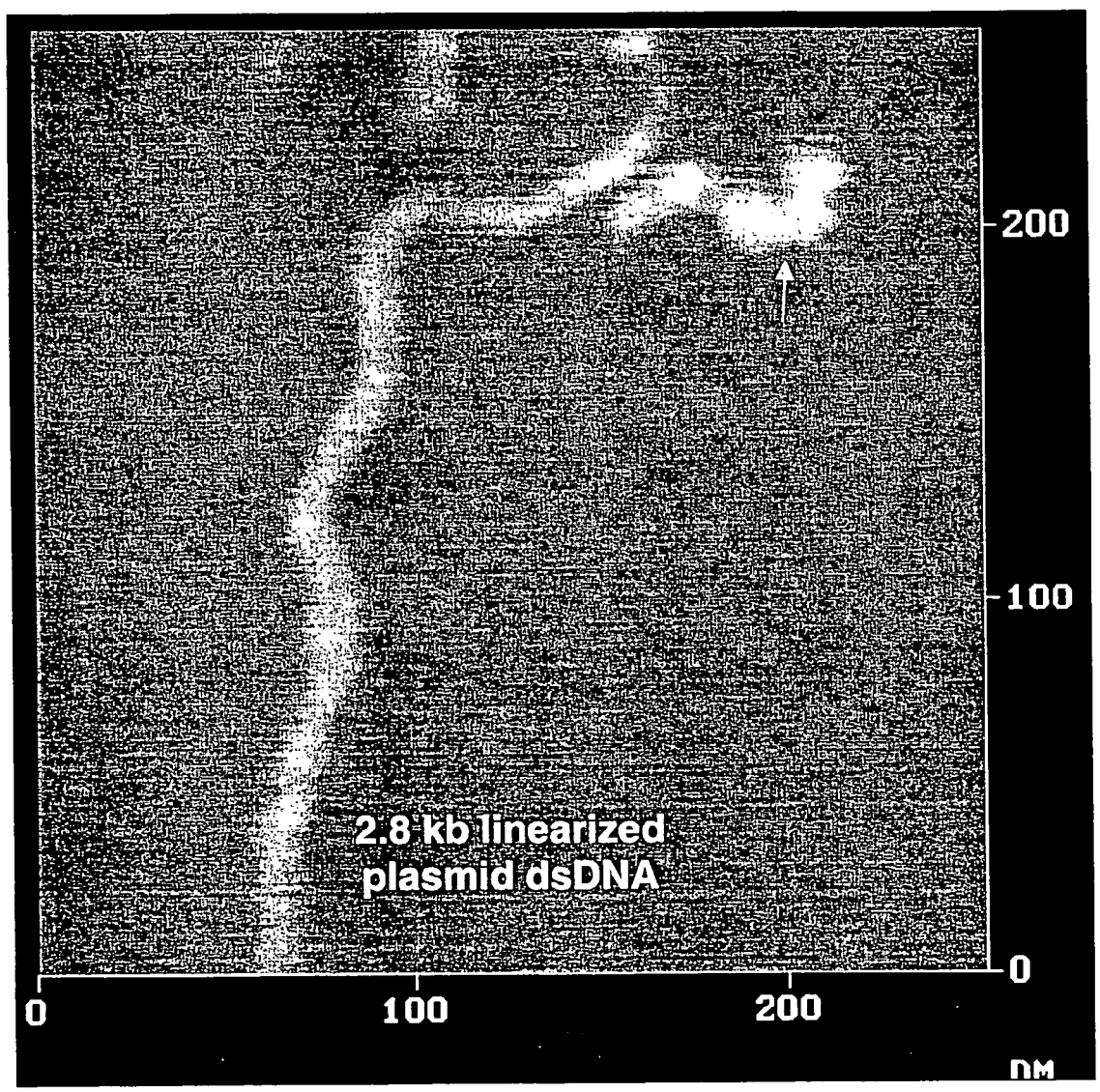
FIG. 15 shows the nano-barcode of FIG. 12 and FIG. 13, imaged by atomic force microscopy (arrow, top right of Figure). For comparison, a 2.8 kb linearized plasmid DNA is also shown.

The exemplary coded probe was imaged by AFM techniques as discussed above. An AFM image of the coded probe is indicated by the arrow in FIG. 15. For comparison, a linearized 2.8 kb plasmid double-stranded DNA molecule is shown adjacent to the coded probe.

All of the METHODS, COMPOSITIONS and APPARATUS disclosed and claimed herein can be made and used without undue experimentation in light of the present disclosure. It will be apparent to those of skill in the art that variations may be applied to the METHODS, COMPOSITIONS and APPARATUS described herein without departing from the concept, spirit and scope of the claimed subject matter. More specifically, it will be apparent that certain agents that are related may be substituted for the agents described herein while the same or similar results would be achieved. All such similar substitutes and modifications apparent to those skilled in the art are deemed to be within the spirit, scope and concept of the claimed subject matter.

TABLE 1

Exemplary Nanotag Elements

| Molecules | Vender | MW g/mol | Distinguishable Features |
|---|---|---|---|
| Fullerenes | | | |
| C60 | BuckyUSA | 720.6 | size, shape, low density |
| C70 | BuckyUSA | 840.7 | size, shape, low density |
| C84 | BuckyUSA | 1008.9 | size, shape, low density |
| Metal Center Fullerenes | | | |
| C60La | BuckyUSA | 859.5 | size, shape, high electron density & charge |
| C84La | BuckyUSA | 1147.8 | size, shape, high electron density & charge |
| C60Er | BuckyUSA | 887.5 | size, shape, high electron density & charge |
| C84Er | BuckyUSA | 1176.8 | size, shape, high electron density & charge |
| Fullerene Oxides | | | |
| C60-O | BuckyUSA | 736 | size, shape, low density |
| C70-O | BuckyUSA | 856 | size, shape, low density |
| Bifunctional Fullerenes | | | |
| O-C60-O | BuckyUSA | 752 | size, shape, low density |
| O-C70-O | BuckyUSA | 872 | size, shape, low density |
| P.O.S.S. Polyhedral oligomeric silsesquioxane | Hybrid Plastics | 800-1600 | 800-1600 |
| Octakis pentacyclo octasiloxane hydrate | Aldrich | 1137 | Size, shape, charge (−) |
| OctaAmmonium POSS | Hybrid Plastics | | Size, shape, charge (+) |
| OctaIsobutyl POSS | Hybrid Plastics | | size, shape |
| OctaMethyl POSS | Hybrid Plastics | | size, shape |
| Octa TmA POSS | Hybrid Plastics | | size, shape, density |
| Organometallics | | | |
| Metal Centers include: Cr, Fe, Al, B, Co, Ni, Zr, Cu, Mg, Zn and Ru. Organic moieties include any functionalizable structure including, sepulcrates, bipyridines, porphrines, corrins, EDTA, biphenyl, benzene, phthalocyanine, hematoporphyrin, heme, naphthalocyanine, phthalocyanine, Cyclopentadiene, Indene, Fluorene, Benzoindene, 4-Fluorophenyl, 4-Methoxypheny, Tris(4-chlorophenyl) and others | Aldrich, Acros, Boulder Scientific | | Metal centers have different size of outer orbital, density, charge distribution, and redox states. The organic moieties impart size, shape and density characteristics. |
| Cu II trifluoroacetyl acetate | Aldrich | | |
| Cu II phthalocyanine | Aldrich | | |
| Co II phthalocyanine | Aldrich | | |
| Fe II phthalocyanine | Aldrich | | |
| Zn II phthalocyanine | Aldrich | | |
| Ni II phthalocyanine | Aldrich | | |
| Mg II phthalocyanine | Aldrich | | |
| Co II 2-3 naphthalocyanine | Aldrich | | |

TABLE 1-continued

Exemplary Nanotag Elements

| Molecules | Vender | MW g/mol | Distinguishable Features |
|---|---|---|---|
| 1,1'-Ferrocenedicarboxylic acid | Aldrich | 274.06 | |
| Co III sepulcrate trichloride | Aldrich | | |
| Cu II 2-pyrazinecarboxylate | Aldrich | | |
| Nano-crystal particle (Ag), NHS esters | Nanoprobes | | |

TABLE 2

Potential Subunits for Backbone Mediated Synthesis

| Candidate | Monofunctionalized | Attachment to subunit |
|---|---|---|
| C60 | C60COOH | Lysine |
| C70 | C70COOH | Lysine |
| La Buckey | LA Bucky COOH | Lysine |
| C60 | C60COOH | Ethyl amino Thymidine |
| C70 | C70COOH | Ethyl amino Thymidine |
| La Buckey | LA Bucky COOH | Ethyl amino Thymidine |
| (NH2)8 POSS | NA | Glutamic or aspartic acid |
| Metal Phalocyanonine | COOH | Lysine or NH2-Thymidine |
| Metal Phalocyanonine | NH2 | Glutamic or aspartic acid |

TABLE 3

Exemplary Subunits for Polymer Decoration

| Tag Element | Mono-functionalized | Attachemnt to polymer subunit | Polymer sequence |
|---|---|---|---|
| C60 | C60COOH | Lysine | $NH_2$-(Gly-Gly-Gly-Lys)$_8$-COOH (SEQ ID NO: 16) |
| C60 | C60COOH | Lysine | NH2-(A-A-A-A-A-A-K)$_7$-COOH (SEQ ID NO: 17) |
| C70 | C70COOH | Lysine | $NH_2$-(Gly-Gly-Gly-Lys)$_8$-COOH (SEQ ID NO: 16) |
| C70 | C70COOH | Lysine | $NH_2$-(A-A-A-A-A-A-K)$_7$-COOH (SEQ ID NO: 17) |
| La Buckey | LA Buckey COOH | Lysine | $NH_2$-(Gly-Gly-Gly-Lys)$_8$-COOH (SEQ ID NO: 16) |
| La Buckey | LA Buckey COOH | Lysine | $NH_2$-(A-A-A-A-A-A-K)$_7$-COOH (SEQ ID NO: 17) |
| C60 | C60COOH | Ethyl amino Thymidine (X) | 5'-(T-X)10-3' |
| C60 | C60COOH | Ethyl amino Thymidine (X) | 5'-(X-Q) where Q is 12 atom spacer |
| C70 | C70COOH | Ethyl amino Thymidine (X) | 5'-(T-X)10-3' |
| C70 | C70COOH | Ethyl amino Thymidine (X) | 5'-(X-Q) where Q is 12 atom spacer |
| La Buckey | LA Buckey COOH | Ethyl amino Thymidine (X) | 5'-(T-X)10-3' |
| La Buckey | LA Buckey COOH | Ethyl amino Thymidine (X) | 5'-(X-Q) where Q is 12 atom spacer |
| $(NH_2)_8$POSS | NA | Glutamic or aspartic acid | $NH_2$-(Gly-Gly-Gly-Glu)$_8$-COOH (SEQ ID NO: 18) |
| $(NH_2)_8$POSS | NA | Glutamic or aspartic acid | $NH_2$-(A-A-A-A-A-E)$_7$-COOH (SEQ ID NQ-19) |
| $(NH_2)_8$POSS | NA | T carboxylate analog (Y) | 5'-(T-Y)10-3' |
| Metal Phalocyanine | COOH | Lysine | $NH_2$-(A-A-A-A-A-A-K)$_7$-COOH (SEQ ID NO: 17) |
| Metal Phalocyanine | COOH | Lysine | $NH_2$-(Gly-Gly-Gly-Lys)$_8$-COOH (SEQ ID N0: 16) |

TABLE 4

Exemplary Subunits for Direct Polymer Imaging

| Subunit | Polymer |
|---|---|
| Lysine (K) | (A$_6$-K)$_8$ (SEQ ID NO:19) or (AAKAAAK)$_4$ (SEQ ID NO: 26) or KKKKKKK (SEQ ID NO: 22) |
| Glutalmic acid(E) | (A$_6$-E)$_8$ (SEQ ID NO: 19) or (AAEAAAE)$_4$ (SEQ ID NO: 26) or EEEEEE (SEQ ID NO: 25) |
| E and K | (AAKAAAE)$_4$ (SEQ ID NO: 26) |
| Br-T (Br) | T-Br-T-Br-TTT-Br-TTT-Br-Br-T (SEQ ID NO: 27) |
| NH$_2$-T (N) | T-N-T-N-TTT-N-TTT-N-N-T (SEQ ID NO: 28) |
| Br and N | T-Br-T-N-T-Br-Br-TTT-N-N-Br-T (SEQ ID NO: 29) |
| Phosphate and spacers | TTT-3-9-3-3-9-9-3-9 |

What is claimed is:

1. A system for nucleic acid sequencing comprising:
  a) a scanning probe microscope;
  b) a surface comprising microfluidic channels;
  c) at least two coded probes attached to the surface, the at least two coded probes comprising two or more identifiably different nano-barcodes that can generate different detectable signals and each of the coded probes comprising a probe molecule attached to at least one of the nano-barcodes, wherein the nano-barcodes are selected from the group consisting of carbon nanotubes, fullerenes, submicrometer metallic barcodes, nanoparticles, quantum dots, combinations thereof, and the nano-barcodes made from nano-tag elements;
  d) one or more target molecules ligated to the at least two coded probes, wherein the coded probes bind to different locations on the target molecules and are adjacent each other on the target molecules, ligated coded probes are formed by ligating the coded probes, and the microfludic channels are configured to align the ligated coded probes such that the ligated coded probes are aligned in the direction of microfluidic flow in the microfluidic channels and organized on the surface by molecular combing; and
  e) a free-flow electrophoresis device that is configured to align a plurality of coded probes on the surface of a substrate.

2. The system of claim 1, wherein the coded probes comprise ligated oligonucleotides.

3. The system of claim 1, wherein the scanning probe microscope is an atomic force microscope or a scanning tunneling microscope.

4. The system of claim 1, the system further comprises a ligase that is used to ligate the coded probes that are adjacent one another on the target molecules to form the ligated coded probes wherein the coded probes comprise oligonucleotides and organized coded probes are formed by aligning the ligated coded probes on the surface by the molecular combing using the microfluidic channels.

5. The system of claim 4, wherein the system is configured to identify the organized coded probes and detect the one or more target molecules based on the organized coded probes.

6. The system of claim 5, wherein the target molecules are proteins or peptides or glycoproteins or lipoproteins or nucleic acids or polynucleotides or oligonucleotides.

7. The system of claim 6, further comprising a library of coded probes comprising all possible sequences for a particular length of oligonucleotide.

8. The system of claim 6, wherein the nucleic acids are attached to the surface.

9. The system of claim 6, wherein the system further comprises an oligonucleotide library.

10. The system of claim 1, wherein the scanning probe microscope comprises an equipment selected from the group consisting of atomic force microscopy, scanning tunneling microscopy, lateral force microscopy, chemical force microscopy, force modulation imaging microscopy, magnetic force microscopy, high frequency magnetic force microscopy, magnetoresistive sensitivity mapping microscopy, electric force microscopy, scanning capacitance microscopy, scanning spreading resistance microscopy, tunneling atomic force microscopy and conductive atomic force microscopy.

* * * * *

SEQUENCE LISTING

<160> NUMBER OF SEQ ID NOS: 29

<210> SEQ ID NO 1
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 1

Ala Ala Met Ala Ala Lys Ala Met Ala Ala Met Ala Lys Ala Val Ala
1               5                   10                  15

Met Ala Ala Lys Ala Val Ala Ala Met Ala Lys Ala Ala Ala
            20                  25                  30

<210> SEQ ID NO 2
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 2

Gly Ala Leu Tyr Ala Met Ala Arg Ala Val His Ala Met Ala Glu Ala
1               5                   10                  15

Ala Cys Gln Ala Ala Trp Ala Met Gly
            20                  25

<210> SEQ ID NO 3
<211> LENGTH: 40
<212> TYPE: DNA
<213> ORGANISM: Artificial Sequence
<220> FEATURE:
<223> OTHER INFORMATION: Synthetic Oligonucleotide

<400> SEQUENCE: 3
ttgggtacac ttacctggta ccccacccgg agttaggggc                           40

<210> SEQ ID NO 4
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 4
gcccctaact gtggaaaatc gatgggcccg cggccgctct tatggttgct gactagacca    60

<210> SEQ ID NO 5
<211> LENGTH: 70
<212> TYPE: DNA
<213> ORGANISM: Artificial Sequence
<220> FEATURE:
<223> OTHER INFORMATION: Synthetic Oligonucleotide

<400> SEQUENCE: 5
tggtctagtc agcaaccata agaagtactc tcgagaagct ttttgaattc tttggatcca    60
tggggcggag    70

<210> SEQ ID NO 6
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 6
ctccgcccca ctagtgtcga cctgcaggcg cgcgagctcc aatgggcgga caatggcaca    60

<210> SEQ ID NO 7
<211> LENGTH: 70
<212> TYPE: DNA
<213> ORGANISM: Artificial Sequence
<220> FEATURE:
<223> OTHER INFORMATION: Synthetic Oligonucleotide

<400> SEQUENCE: 7
tgtgccattg tccgcccatt agcttttgtt ccctttagtg agggttaatt tcgagcttgg    60
attgagatgc    70

<210> SEQ ID NO 8
<211> LENGTH: 60
<212> TYPE: PRT
<213> ORGANISM: Artificial Sequence
<220> FEATURE:
<223> OTHER INFORMATION: Synthetic Oligonucleotide

<400> SEQUENCE: 8

Gly Cys Ala Thr Cys Thr Cys Ala Ala Thr Cys Gly Thr Ala Ala Thr
 1               5                  10                  15

Cys Ala Ala Gly Gly Thr Cys Ala Thr Ala Gly Cys Thr Gly Thr Thr
            20                  25                  30

Thr Cys Cys Thr Gly Thr Gly Thr Thr Thr Gly Cys Ala Thr Ala Cys
        35                  40                  45

Thr Thr Cys Thr Gly Cys Cys Ala Thr Thr Cys Gly
    50                  55                  60

<210> SEQ ID NO 9
<211> LENGTH: 70
<212> TYPE: DNA
<213> ORGANISM: Artificial Sequence
<220> FEATURE:
<223> OTHER INFORMATION: Synthetic Oligonucleotide

<400> SEQUENCE: 9
cgaatggcag aagtatgcaa gaaattgtta tccgctcaca attccacaca atatacgagc    60
tgctggggag    70

<210> SEQ ID NO 10
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 10
ctccccagca cggaagtata aagtgtaaag cctggggtgc ggatgggcgg aatgagactg     60

<210> SEQ ID NO 11
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 11
acagtctcat tccgcccatc cctaatgagt gagctaactc acagtaattg cggctagcgg     60
a                                                                    61

<210> SEQ ID NO 12
<211> LENGTH: 74
<212> TYPE: DNA
<213> ORGANISM: Artificial Sequence
<220> FEATURE:
<223> OTHER INFORMATION: Synthetic Oligonucleotide

<400> SEQUENCE: 12
tcgagagtac ttctagagcg gccgcgggcc catcgatttt ccacccgggt ggggtaccag     60
gtaagtgtac ccaa                                                      74

<210> SEQ ID NO 13
<211> LENGTH: 78
<212> TYPE: DNA
<213> ORGANISM: Artificial Sequence
<220> FEATURE:
<223> OTHER INFORMATION: Synthetic Oligonucleotide

<400> SEQUENCE: 13
ctcactaaag ggaacaaaag ctggagctcg cgcgcctgca ggtcgacact agtggatcca     60
aagaattcaa aaagcttc                                                  78

<210> SEQ ID NO 14
<211> LENGTH: 74
<212> TYPE: DNA
<213> ORGANISM: Artificial Sequence
<220> FEATURE:
<223> OTHER INFORMATION: Synthetic Oligonucleotide

<400> SEQUENCE: 14
tggaattgtg agcggataac aatttcacac aggaaacagc tatgaccttg attacgccaa     60
gctcgaaatt aacc                                                      74

<210> SEQ ID NO 15
<211> LENGTH: 84
<212> TYPE: DNA
<213> ORGANISM: Artificial Sequence
<220> FEATURE:
<223> OTHER INFORMATION: Synthetic Oligonucleotide

```
<400> SEQUENCE: 15
tccggtagcc gcaattactg tgagttagct cactcattag gcaccccagg ctttacactt    60
tatacttccg gctcgtatat tgtg                                           84

<210> SEQ ID NO 16
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 16

Gly Gly Gly Lys Gly Gly Gly Lys Gly Gly Gly Lys Gly Gly Gly Lys
1               5                   10                  15

Gly Gly Gly Lys Gly Gly Gly Lys Gly Gly Gly Lys Gly Gly Gly Lys
            20                  25                  30

<210> SEQ ID NO 17
<211> LENGTH: 49
<212> TYPE: PRT
<213> ORGANISM: Artificial Sequence
<220> FEATURE:
<223> OTHER INFORMATION: Synthetic Peptide

<400> SEQUENCE: 17

Ala Ala Ala Ala Ala Ala Lys Ala Ala Ala Ala Ala Lys Ala Ala
1               5                   10                  15

Ala Ala Ala Ala Lys Ala Ala Ala Ala Ala Lys Ala Ala Ala Ala
            20                  25                  30

Ala Ala Lys Ala Ala Ala Ala Ala Lys Ala Ala Ala Ala Ala
        35                  40                  45

Lys

<210> SEQ ID NO 18
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 18

Gly Gly Gly Glu Gly Gly Gly Glu Gly Gly Gly Glu Gly Gly Gly Glu
1               5                   10                  15

Gly Gly Gly Glu Gly Gly Gly Glu Gly Gly Gly Glu Gly Gly Gly Glu
            20                  25                  30

<210> SEQ ID NO 19
<211> LENGTH: 42
<212> TYPE: PRT
<213> ORGANISM: Artificial Sequence
<220> FEATURE:
<223> OTHER INFORMATION: Synthetic Peptide

<400> SEQUENCE: 19

Ala Ala Ala Ala Ala Glu Ala Ala Ala Ala Ala Glu Ala Ala Ala Ala
1               5                   10                  15

Ala Glu Ala Ala Ala Ala Ala Glu Ala Ala Ala Ala Ala Glu Ala Ala
            20                  25                  30

Ala Ala Ala Glu Ala Ala Ala Ala Ala Glu
        35                  40
```

<210> SEQ ID NO 20
<211> LENGTH: 63
<212> TYPE: PRT
<213> ORGANISM: Artificial Sequence
<220> FEATURE:
<223> OTHER INFORMATION: Synthetic Peptide

<400> SEQUENCE: 20

```
Ala Ala Ala Ala Ala Ala Lys Ala Ala Ala Ala Ala Lys Ala Ala
1               5                   10                  15

Ala Ala Ala Ala Lys Ala Ala Ala Ala Ala Lys Ala Ala Ala Ala
            20                  25                  30

Ala Ala Lys Ala Ala Ala Ala Ala Lys Ala Ala Ala Ala Ala Ala
        35                  40                  45

Lys Ala Ala Ala Ala Ala Ala Lys Ala Ala Ala Ala Ala Ala Lys
    50                  55                  60
```

<210> SEQ ID NO 21
<211> LENGTH: 29
<212> TYPE: PRT
<213> ORGANISM: Artificial Sequence
<220> FEATURE:
<223> OTHER INFORMATION: Synthetic Peptide

<400> SEQUENCE: 21

```
Ala Ala Lys Ala Ala Ala Lys Ala Ala Lys Ala Ala Ala Lys Ala
1               5                   10                  15

Ala Lys Ala Ala Ala Lys Ala Ala Lys Ala Ala Ala Lys
            20                  25
```

<210> SEQ ID NO 22
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 22

```
Lys Lys Lys Lys Lys Lys Lys
1               5
```

<210> SEQ ID NO 23
<211> LENGTH: 58
<212> TYPE: PRT
<213> ORGANISM: Artificial Sequence
<220> FEATURE:
<223> OTHER INFORMATION: Synthetic Peptide

<400> SEQUENCE: 23

```
Ala Ala Ala Ala Ala Ala Glu Ala Ala Ala Ala Ala Glu Ala Ala
1               5                   10                  15

Ala Ala Ala Ala Glu Ala Ala Ala Ala Ala Glu Ala Ala Ala Ala
            20                  25                  30

Ala Ala Ala Ala Glu Ala Ala Ala Ala Ala Glu Ala Ala Ala Ala
        35                  40                  45

Ala Ala Glu Ala Ala Ala Ala Ala Ala Glu
    50                  55
```

<210> SEQ ID NO 24
<211> LENGTH: 28
<212> TYPE: PRT
<213> ORGANISM: Artificial Sequence
<220> FEATURE:
<223> OTHER INFORMATION: Synthetic Peptide

```
<400> SEQUENCE: 24

Ala Ala Glu Ala Ala Ala Glu Ala Ala Glu Ala Ala Glu Ala Ala
1               5                   10                  15

Glu Ala Ala Ala Glu Ala Ala Glu Ala Ala Ala Glu
            20                  25

<210> SEQ ID NO 25
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 25

Glu Glu Glu Glu Glu Glu
1               5

<210> SEQ ID NO 26
<211> LENGTH: 28
<212> TYPE: PRT
<213> ORGANISM: Artificial Sequence
<220> FEATURE:
<223> OTHER INFORMATION: Synthetic Peptide

<400> SEQUENCE: 26

Ala Ala Lys Ala Ala Ala Glu Ala Ala Lys Ala Ala Ala Glu Ala Ala
1               5                   10                  15

Lys Ala Ala Ala Glu Ala Ala Lys Ala Ala Ala Glu
            20                  25

<210> SEQ ID NO 27
<211> LENGTH: 14
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: modified_base
<222> LOCATION: (2)..(2)
<223> OTHER INFORMATION: Bromothymidine
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: modified_base
<222> LOCATION: (4)..(4)
<223> OTHER INFORMATION: Bromothymidine
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: modified_base
<222> LOCATION: (8)..(8)
<223> OTHER INFORMATION: Bromothymidine
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: modified_base
<222> LOCATION: (12)..(13)
<223> OTHER INFORMATION: Bromothymidine
<220> FEATURE:
<221> NAME/KEY: misc_feature
<222> LOCATION: (12)..(13)
<223> OTHER INFORMATION: n is a, c, g, or t
```

```
<400> SEQUENCE: 27
tntntttntt tnnt                                                      14

<210> SEQ ID NO 28
<211> LENGTH: 14
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: modified_base
<222> LOCATION: (2)..(2)
<223> OTHER INFORMATION: Aminothymidine
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: modified_base
<222> LOCATION: (4)..(4)
<223> OTHER INFORMATION: Aminothymidine
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: modified_base
<222> LOCATION: (8)..(8)
<223> OTHER INFORMATION: Aminothymidine
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: modified_base
<222> LOCATION: (12)..(13)
<223> OTHER INFORMATION: Aminothymidine
<220> FEATURE:
<221> NAME/KEY: misc_feature
<222> LOCATION: (12)..(13)
<223> OTHER INFORMATION: n is a, c, g, or t

<400> SEQUENCE: 28
tntntttntt tnnt                                                      14

<210> SEQ ID NO 29
<211> LENGTH: 14
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: modified_base
<222> LOCATION: (2)..(2)
<223> OTHER INFORMATION: Bromothymidine
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: modified_base
<222> LOCATION: (4)..(4)
<223> OTHER INFORMATION: Aminothymidine
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: modified_base
<222> LOCATION: (6)..(7)
<223> OTHER INFORMATION: Bromothymidine
<220> FEATURE:
<221> NAME/KEY: misc_feature
<222> LOCATION: (6)..(7)
<223> OTHER INFORMATION: n is a, c, g, or t
```

```
-continued

<220> FEATURE:
<221> NAME/KEY: modified_base
<222> LOCATION: (11)..(12)
<223> OTHER INFORMATION: Aminothymidine
<220> FEATURE:
<221> NAME/KEY: misc_feature
<222> LOCATION: (11)..(13)
<223> OTHER INFORMATION: n is a, c, g, or t
<220> FEATURE:
<221> NAME/KEY: modified_base
<222> LOCATION: (13)..(13)
<223> OTHER INFORMATION: Bromothymidine

<400> SEQUENCE: 29
tntntnnttt nnnt                                                         14
```